United States Patent

Inaba et al.

[11] Patent Number: 5,885,757
[45] Date of Patent: Mar. 23, 1999

[54] AMINOPOLYCARBOXYLIC ACID CHELATING AGENT, HEAVY METAL CHELATE COMPOUND THEREOF, PHOTOGRAPHIC ADDITIVE AND PROCESSING METHOD

[75] Inventors: Tadashi Inaba; Kiyoshi Morimoto; Shigeo Hirano, all of Minami-ashigara, Japan

[73] Assignee: Fuji Photo Film Co., Ltd., Minami-ashigara, Japan

[21] Appl. No.: 960,559

[22] Filed: Oct. 29, 1997

[30] Foreign Application Priority Data

Oct. 31, 1996 [JP] Japan ................................... 8-289635

[51] Int. Cl.$^6$ .................................................. G03C 7/42
[52] U.S. Cl. ............................................ 430/430; 430/393
[58] Field of Search ....................................... 430/430, 393

[56] References Cited

U.S. PATENT DOCUMENTS

| | | | |
|---|---|---|---|
| 5,183,590 | 2/1993 | Carter et al. ............................ | 252/392 |
| 5,338,649 | 8/1994 | Inaba et al. ............................. | 430/430 |
| 5,547,817 | 8/1996 | Okada et al. ........................... | 430/393 |
| 5,580,705 | 12/1996 | Ueda et al. ............................. | 430/430 |
| 5,635,341 | 6/1997 | Yamashita et al. .................... | 430/430 |
| 5,679,501 | 10/1997 | Seki et al. ............................... | 430/393 |

FOREIGN PATENT DOCUMENTS

| | | |
|---|---|---|
| 532003 | 3/1993 | European Pat. Off. . |
| 590879 | 4/1994 | European Pat. Off. . |
| 743558 | 11/1996 | European Pat. Off. . |
| 762203 | 3/1997 | European Pat. Off. . |
| 6059422 | 3/1994 | Japan . |
| WO96/35662 | 11/1986 | WIPO . |
| WO94/28464 | 12/1994 | WIPO . |

OTHER PUBLICATIONS

Chemical Abstracts, vol. 106, No. 18, May 4, 1987, 106:144901z.
Chemical Abstracts, vol. 112, No. 15, Apr. 9, 1990, 112:138185b.
Chemical Abstracts, vol. 116, No. 10, Mar. 9, 1992, 116:92508m.

*Primary Examiner*—Hoa Van Le
*Attorney, Agent, or Firm*—Burns, Doane, Swecker & Mathis, LLP

[57] ABSTRACT

An aminopolycarboxylic acid compound represented by the following formula or analogous thereof:

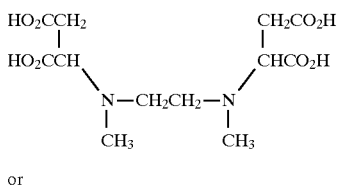

or

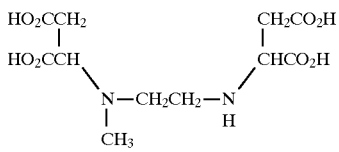

The aminopolycarboxylic acid compound of the present invention can be used as a chelating agent for various metals, which is excellent in the biodegradability and masking effect on metals.

9 Claims, No Drawings

AMINOPOLYCARBOXYLIC ACID CHELATING AGENT, HEAVY METAL CHELATE COMPOUND THEREOF, PHOTOGRAPHIC ADDITIVE AND PROCESSING METHOD

BACKGROUND OF THE INVENTION

The present invention relates to an aminopolycarboxylic acid chelating agent, heavy metal chelate compound thereof and method for processing silver halide photosensitive materials with them. In particular, the present invention relates to a novel chelating agent for masking metal ions harmful to new bleaching agents and photographic processing agents used in a bleaching or bleach-fixing step after the treatment with a color developer.

Photosensitive materials are exposed, color-developed and then processed with a processing solution having a bleaching function. As the bleaching agents contained in the processing solution having the bleaching function, ferric complex salts are widely known. Among the ferric complex salts, ferric complex salts of ethylenediaminetetraacetic acid (EDTA) has been known from old times. Ferric complex salt of 1,3-propanediaminetetraacetate (1,3-PDTA) having a stronger bleaching function has been widely used since several years ago. Although the rapid processing properties of ferric complex salt of 1,3-PDTA are superior to those of ferric complex salt of EDTA, the bleach fog is easily caused by a strong oxidizing power thereof, and the image-storability after the process is easily impaired (magenta stain is increased). Another problem is that because of a high oxidation-reduction potential, the decomposition is accelerated with time in a thiosulfuric acid-containing system to form sulfur. As the recognition of the global environmental safeguards is being improved recently, a bleaching agent usable in place of difficultly biodegradable ferric complex salt of EDTA and ferric complex salt of 1,3-PDTA is being developed in the photographic field in which the development of a processing agent which causes as low as possible environmental pollution demanded. The metal complex salts are usable not only as a component of a composition of a bleach-processing solution but also as that of an after-treating composition used for the intensification, reduction or toning. However, they also have the problem of the poor biodegradation.

As the compounds capable of solving these problems, those described in Japanese Patent Unexamined Publication (hereinafter referred to as "J.P. KOKAI") Nos. Hei 5-72695 and 5-303186 were developed. However, it has been found that when such a compound is used, another problem occurs in some cases. For example, when a ferric complex of ethylenediaminebissuccinic acid (EDDS) described therein is used as the bleach-fixing agent, problems such as insufficient recoloring and Blix discoloration occur. A further effort must be made for solving this problem.

As the photographic process is conducted at various places ranging from a large-scale processing laboratories having a large automatic developing machine to a photo processing shops called "mini-labs" having a small automatic developing machine, the processing efficiency tends to be lowered in some cases.

One of the main causes of this problem is the contamination of the processing solution with a metal ion. The ill effects of the incorporated metal ion, which vary depending on the kind of the ion and processing solution, are the clogging of a filter in the circulation system of the automatic developer, staining of the film in the course of the process and decomposition of a color developing agent, black developing agent such as hydroquinone or monol and a preservative such as a hydroxylamine or sulfite. As a result, the photographic properties are seriously impaired.

A chelating agent which masks the metal ion has been used for solving the above-described problems in the art. The chelating agents include, for example, aminopolycarboxylic acids (such as ethylenediaminetetraacetic acid and diethylenetriaminepentaacetic acid) described in Japanese Patent Publication for Opposition Purpose (hereinafter referred to as "J.P. KOKOKU") Nos. Sho 48-30496 and 44-30232; organophosphonic acids described in J.P. KOKAI Nos. Sho 56-97347 and 56-39359 and West German Patent No. 2,227,639; phosphonocarboxylic acids described in J.P. KOKAI Nos. Sho 52-102726, 53-42730, 54-121127, 55-126241 and 55-65956; and compounds described in J.P. KOKAI Nos. Sho 58-195845 and 58-203440 and J.P. KOKOKU No. sho 53-40900. Although some of these compounds have already been practically used, the efficiency of them was not yet satisfactory.

Compounds having a skeleton similar to that of the compounds of the present invention include ethylenediamine-N,N'-disuccinic acid described on pages 309 to 311 of "Chelate Kagaku (Chelate Chemistry)" (5) written by Kagehei Ueno and published by Nanko-do.

The masking capacity of this compound is easily variable depending on pH and, therefore, the capacity is not on a satisfactory level when the conditions of the treating solution are varied in many cases. Particularly in an alkaline developing bath in which the masking capacity of this compound for iron ion is essentially low, an excess amount of the compound is necessitated, which is photographically undesirable. Particularly, as the social demand of the environmental protection is increasing recently, the amount of the replenisher for the photographic processing solution is being further decreased and, therefore, the residence time of the processing solution in the processing machine becomes longer. In addition, as the rapid process is demanded, the concentration of the developing agent, bleaching agent and fixing agent tends to be increased and the temperature of the processing solution also tends to be elevated. Thus the deterioration in the long-time storability is becoming serious.

Further, as the concentration of the processing solution is increased for the purpose of accelerating the process, the changes of the conditions (mainly pH) become more serious. As a result, the effect of the metal-masking agent is reduced disadvantageously. Under these circumstances, the development of a more excellent, new chelating agent capable of effectively masking the metal even under unstable conditions is demanded.

SUMMARY OF THE INVENTION

Therefore, the first object of the present invention is to provide a chelating agent for various metals, which is excellent in the biodegradability and masking effect on metals.

The second object is to provide a heavy metal chelate compound for heavy metals, which is excellent in the biodegradability.

The third object is to provide a photographic processing composition which does not form a precipitate or sludge even when it is contaminated with a metal ion.

The fourth object is to provide a processing composition capable of keeping its properties even under severe conditions caused by the elevation of the temperature of the processing composition or by the prolongation of the residence time of the processing solution; and a processing method wherein the processing composition is used.

The fifth object is to provide a processing composition excellent in the desilvering properties and image-storability after the process and free from a bleach fog, and a desilvering process wherein this composition is used.

The sixth object is to provide a processing composition which does not cause the problems such as poor recoloring and Blix discoloration and also a desilvering process wherein this composition is used.

These and other objects of the present invention will be apparent from the following description and examples.

After investigations on the above-described problems, the inventors have found that the objects of the invention can be attained by the following aminopolycarboxylic acid chelating agent and a heavy metal chelate compound thereof, and a method for processing silver halide photosensitive materials with the compound. Namely, the present invention provides:

(1) a compound represented by the following general formula (I):

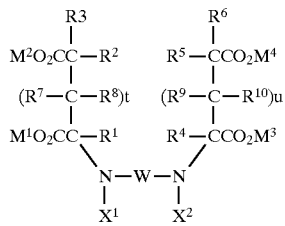

wherein $R^1$, $R^2$, $R^3$, $R^4$, $R^5$, $R^6$, $R^7$, $R^8$, $R^9$ and $R^{10}$ each represent a hydrogen atom, aliphatic group, aromatic group or hydroxyl group, W represents a divalent connecting group wherein the main chain has at most 5 carbon atoms, $X^1$ represents a hydrogen atom, alkyl group, hydroxyethyl group, alkoxyalkyl group, aralkyl group or hydroxyl group, $X^2$ represents an alkyl group, aralkyl group, hydroxyl group, hydroxyalkyl group or alkoxyalkyl group, $M^1$, $M^2$, $M^3$ and $M^4$ each represent a hydrogen atom or cation, and t and u each represent 0, (2) a heavy metal chelate compound of the compound represented by the general formula (I) in above item (1), (3) a chelating agent which comprises the compound represented by the general formula (I) in above item (1), (4) a photographic additive which comprises the compound represented by the general formula (I) in above item (1) (wherein t and u each represent an integer of 0 to 5) or a heavy metal chelate compound thereof, and (5) a method for processing a silver halide photosensitive material, characterized by processing an imagewise-exposed silver halide photosensitive material in the presence of at least one compound selected from the compounds of the above general formula (I) (wherein t and u each represent an integer of 0 to 5) and the heavy metal chelate compounds thereof.

The structure of the general formula (I) is characterized in that one or two of unsubstituted alkyl groups, aralkyl groups, hydroxyl group, hydroxyethyl and alkoxyalkyl groups are introduced on N and N' of the aminopolycarboxylic acid. Although secondary amines having no substituent on N and N' were disclosed hitherto (J.P. KOKAI Nos. Hei 5-303186, 6-110168, 6-130612, 6-130587, etc.), the above-described problems have not yet been solved by these compounds as the bleaching agents. Also when such a compound is used as the chelating agent (only the metal-free chelating part is used), the above-described problems in the masking of metals cannot be solved. Thus, it has been unexpected that the problem can be solved by introducing an unsubstituted alkyl group, aralkyl group, hydroxyl group, hydroxyethyl group or alkoxyalkyl group on N and N'.

DESCRIPTION OF THE PREFERRED EMBODIMENTS:

The detailed description will be made on the compounds of the general formula (I).

The aliphatic groups represented by $R^1$, $R^2$, $R^3$, $R^4$, $R^5$, $R^6$, $R^7$, $R^8$, $R^9$ and $R^{10}$ are linear, branched or cyclic alkyl, alkenyl or alkynyl groups, and those having 1 to 10 carbon atoms are preferred. The aliphatic groups are preferably alkyl groups, more preferably alkyl groups having 1 to 4 carbon atoms, and particularly preferably methyl and ethyl groups. The aromatic groups represented by $R^1$, $R^2$, $R^3$, $R^4$, $R^5$, $R^6$, $R^7$, $R^8$, $R^9$ and $R^{10}$ are monocyclic or bicyclic aryl groups such as phenyl and naphthyl groups. The phenyl group is preferred. The aliphatic groups and aromatic groups represented by $R^1$, $R^2$, $R^3$, $R^4$, $R^5$, $R^6$, $R^7$, $R^8$, $R^9$ and $R^{10}$ may have a substituent such as, for example, alkyl groups (such as methyl and ethyl), aralkyl groups (such as phenylmethyl), alkenyl groups (such as allyl), alkynyl groups, alkoxyl groups (such as methoxyl and ethoxyl), aryl groups (such as phenyl and p-methylphenyl), amino groups (such as dimethylamino), acylamino groups (such as acetylamino), sulfonylamino groups (such as methanesulfonylamino), ureido group, urethane group, aryloxy groups (such as phenyloxy), sulfamoyl (such as methylsulfamoyl), carbamoyl groups (such as carbamoyl and methylcarbamoyl), alkylthio groups (such as methylthio), arylthio groups (such as phenylthio), sulfonyl groups (such as methanesulfonyl), sulfinyl groups (such as methanesulfinyl), hydroxyl group, halogen atoms (such as chlorine, bromine and fluorine atoms), cyano group, sulfo group, carboxyl group, phosphono group, aryloxycarbonyl groups (such as phenyloxycarbonyl), acyl groups (such as acetyl and benzoyl), alkoxycarbonyl groups (such as methoxycarbonyl), acyloxy groups (such as acetoxy), carbonamido group, sulfonamido group, nitro group and hydroxamic acid group. If possible, dissociation products or salts of them are also usable. When the substituents have carbon atoms, the number of the carbon atoms is preferably 1 to 4. Each of $R^1$, $R^2$, $R^3$, $R^4$, $R^5$, $R^6$, $R^7$, $R^8$, $R^9$ and $R^{10}$ is preferably a hydrogen atom or hydroxyl group. More preferably, $R^1$, $R^2$, $R^4$, $R^5$, $R^7$, $R^8$, $R^9$ and $R^{10}$ is hydrogen atom while $R^3$ and $R^6$ is hydrogen atom or hydroxy group. Most preferably, all of $R^1$, $R^2$, $R^3$, $R^4$, $R^5$, $R^6$, $R^7$, $R^8$, $R^9$ and $R^{10}$ are hydrogen atoms.

The divalent connecting group represented by "W" can be preferably represented by the following general formula (W):

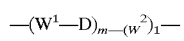

wherein $W^1$ and $W^2$ may be the same or different from each other, and the total carbon atoms in the main chain is at most 5. $W^1$ and $W^2$ represent, for example, linear alkylene groups having 2 to 5 carbon atoms or branched alkylene groups having 2 to 8 carbon atoms (such as ethylene and propylene), cycloalkylene groups having 5 to 10 carbon atoms (such as 1,2-cyclohexyl), arylene groups having 6 to 10 carbon atoms (such as o-phenylene), aralkylene groups having 7 to 10 carbon atoms (such as o-xylenyl) or carbonyl group. D represents —O—, —S—, —N(R$_w$)— or divalent nitrogen-containing heterocyclic group. Preferably, D represents —O—, —S— or —N—(R$_w$)—. R$_w$ represents a hydrogen atom, alkyl group having 1 to 8 carbon atoms (such as methyl) or aryl group having 6 to 10 carbon atoms (such as phenyl) which may be substituted with —COOM$_a$, —PO$_3$M$_b$, M$_c$. —OH or —SO$_3$M$_d$. M$_a$, M$_b$, M$_c$ and M$_d$ each represent a hydrogen atom or cation. The cations include, alkali metals (such as lithium, sodium and potassium), ammoniums (such as ammonium and tetraethylammonium) and pyridinium. Preferably, R$_w$ represents a hydrogen atom or an alkyl group having 1 to 8 carbon atoms. The connecting group represented by "W" may have a substituent. The substituents are, for example, those described above as substituents of R$^1$ through R$^{10}$. The divalent, nitrogen-containing heterocyclic groups are preferably 5- or 6-membered rings wherein the hetero atom is nitrogen. It is further preferred that the carbon atoms adjacent to each other are connected with W$^1$ and W$^2$ as in the imidazolyl group. W$^1$ and W$^2$ are preferably alkylene groups having 2 to 4 carbon atoms. m represents an integer of 0 to 3. When m is 2 or 3, plural W$^1$—D's may be the same or different from each other. m is preferably 0 to 2, more preferably 0 or 1, and particularly 0. "l" represents an integer of 1 to 3. When l is 2 or 3, plural W$^2$'s may be the same or different from each other. l is preferably 1 or 2, and particularly 1. Examples of W include those represented by the following formulae:

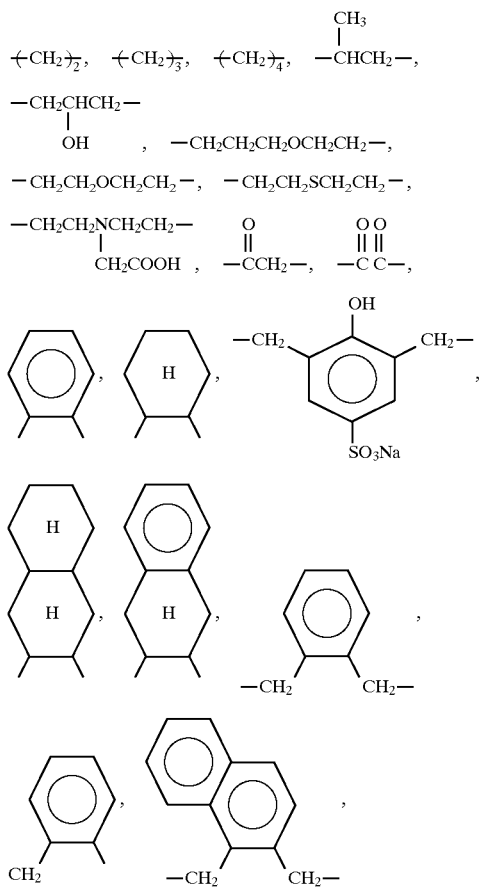

-continued

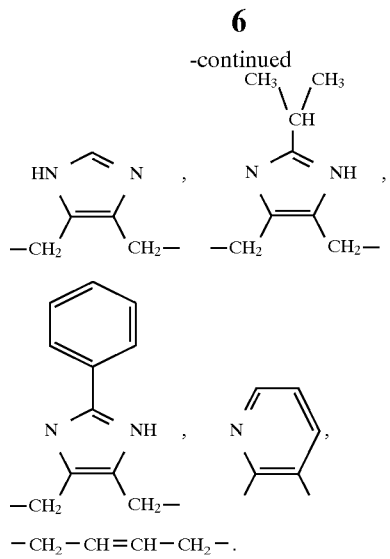

$-CH_2-CH=CH-CH_2-$.

(Unsubstituted) alkyl groups represented by X$^1$ and X$^2$ are linear or branched alkyl groups having 1 to 5 carbon atoms. More preferably, they are linear and particularly methyl or ethyl group. Methyl group is the most preferred. X$^2$ is preferably an alkyl group having 1 to 5 carbon atoms.

The aralkyl group represented by X$^1$ and X$^2$ may have a substituent, if necessary. Unsubstituted aralkyl groups are preferred. The number of carbon atoms is preferably 6 to 12, more preferably 6 to 10, and most preferably 6 to 8. An example of them is phenylmethyl.

The alkoxyalkyl group represented by X$^1$ and X$^2$ is prefereable one wherein the alkoxy has 1 to 6 carbon atoms and the alkyl has 1 to 6 carbon atoms. More preferably, the number of carbon atoms of the alkoxy is 1 to 3 and the number of carbon atoms of the alkyl is 1 to 3. Examples of the alkoxyalkyl group include methoxymethyl, methoxyethyl and ethoxyethyl.

The hydroxyalkyl represented by X$^2$ is prefereably one having 1 to 5 carbon atoms, more preferably hydroxyethyl group.

X$^2$ is preferably a methyl, ethyl, hydroxyethyl and alkoxyalkyl (particularly, methoxymethyl, methoxyethyl and ethoxyethyl) group. Among them, methyl and hydroxyethyl groups are more preferred. Methyl group is the most preferred.

X$^1$ is hydrogen atom and those suitable as X$^2$. Preferably, X$^1$ is hydrogen or an alkyl group having 1 to 5 carbon atoms.

The cation represented by M$^1$, M$^2$, M$^3$ and M$^4$ may be either organic or inorganic cations. When two or more cations are present in a molecule, they may be either the same or different from each other. The cations include, for example, ammoniums (such as ammonium and tetraethylammonium), alkali metals (such as lithium, sodium and potassium), alkaline earth metals (such as calcium, magnesium and barium) and pyridinium. The cations are preferably inorganic cations, more preferably alkali metals.

t and u each represent an integer of 0 to 5, preferablly 0 or 1, and more preferablly 0. When t and u are equal to or more than 2, the groups represented by R$^7$ may be either the same or different from each other. This is the same for R$^8$, R$^9$ and R$^{10}$.

In the compounds represented by the general formula (I), those represented by the following general formula (II) are preferred and those represented by the following general formula (III) are more preferred, and those represented by the general formula (IV) are the most preferred:

$$\begin{array}{c} \text{R}^3 \quad\quad\quad \text{R}^6 \\ | \quad\quad\quad\quad | \\ \text{M}^2\text{O}_2\text{CC}-\text{R}^2 \quad \text{R}^5-\text{C}-\text{CO}_2\text{M}^4 \\ | \quad\quad\quad\quad\quad | \\ (\text{R}^7-\text{CH})_t \quad (\text{R}^9-\text{CH})_u \\ | \quad\quad\quad\quad\quad | \\ \text{M}^1\text{O}_2\text{CC}-\text{R}^1 \quad \text{R}^4-\text{CCO}_2\text{M}^3 \\ * \quad\quad\quad\quad * \\ \diagdown \quad\quad \diagup \\ \text{N}-\text{W}-\text{N} \\ | \quad\quad | \\ \text{X}^1 \quad\quad \text{X}^2 \end{array} \quad (\text{II})$$

wherein $R^1$, $R^2$, $R^3$, $R^4$, $R^5$, $R^6$, $R^7$, $R^9$, W, $X^1$, $X^2$, $M^1$, $M^2$, $M^3$ and $M^4$ are as defined in the above general formula (I), preferred examples of them are also the same as those described above, t and u each represent an integer of 0 to 5, preferred range of them are as described above, and "*" indicates that the carbon having the symbol * is in the absolute configuration with S, $$\begin{array}{c} \text{R}^3 \quad\quad\quad \text{R}^6 \\ | \quad\quad\quad\quad | \\ \text{M}^2\text{O}_2\text{CC}-\text{R}^2 \quad \text{R}^5-\text{CCO}_2\text{M}^4 \\ | \quad\quad\quad\quad | \\ (\text{R}^7-\text{CH})_t \quad (\text{R}^9-\text{CH})_u \\ | \quad\quad\quad\quad | \\ \text{M}^1\text{O}_2\text{CC}-\text{R}^1 \quad \text{R}^4-\text{CCO}_2\text{M}^3 \\ * \quad\quad\quad\quad * \\ \diagdown \quad\quad \diagup \\ \text{N}-\text{W}-\text{N} \\ | \quad\quad | \\ \text{X}^{11} \quad\quad \text{CH}_3 \end{array} \quad (\text{III})$$

wherein $R^1$, $R^2$, $R^3$, $R^4$, $R^5$, $R^6$, $R^7$, $R^9$, W, $M^1$, $M^2$, $M^3$ and $M^4$ are as defined in the general formula (I), preferred examples of them are also the same as those described above, $X^{11}$ represents a hydrogen atom or methyl group, t and u each represent an integer of 0 to 5, preferred range of them are as described above, and "*" indicates that the carbon having the symbol * is in the absolute configuration with S, and $$\begin{array}{c} \text{M}^2\text{O}_2\text{CCH}_2 \quad\quad \text{CH}_2\text{CO}_2\text{M}^4 \\ | \quad\quad\quad\quad | \\ \text{M}^1\text{O}_2\text{CCH} \quad\quad \text{CHCO}_2\text{M}^3 \\ * \quad\quad\quad\quad * \\ \diagdown \quad\quad \diagup \\ \text{N}-\text{W}-\text{N} \\ | \quad\quad | \\ \text{H} \quad\quad \text{CH}_3 \end{array} \quad (\text{IV})$$

wherein W, $M^1$, $M^2$, $M^3$ and $M^4$ are as defined in the general formula (I), preferred examples of them are also the same as those described above, and "*" indicates that the carbon having the symbol * is in the absolute configuration with S.

Examples of the compounds represented by the general formula (I) in the present invention will be given below, which by no means limit the invention.

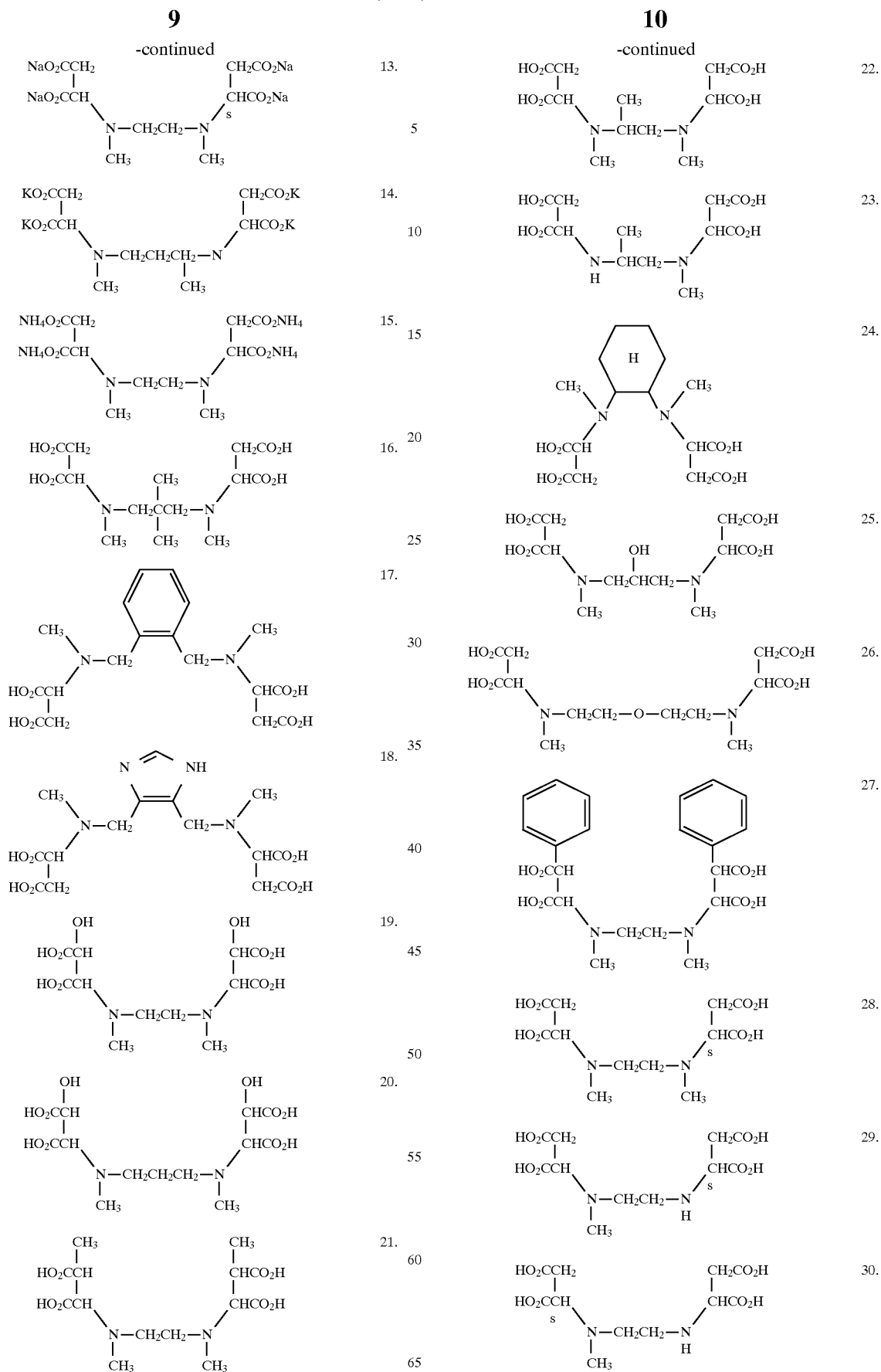

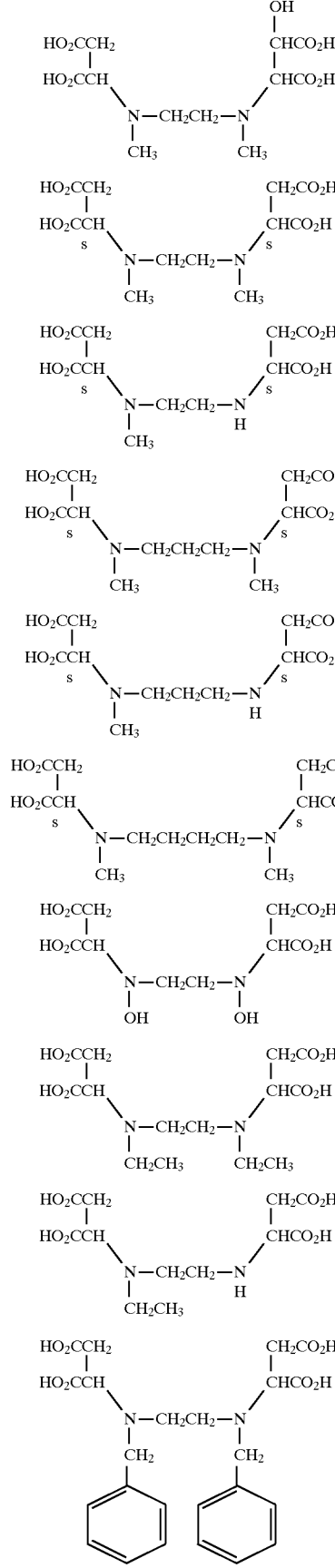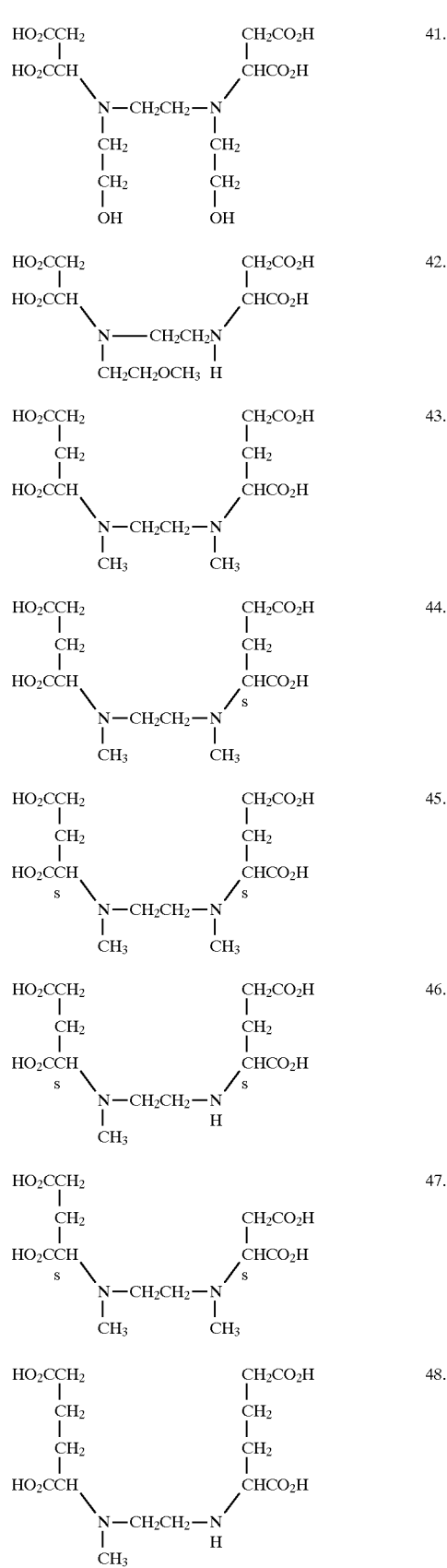

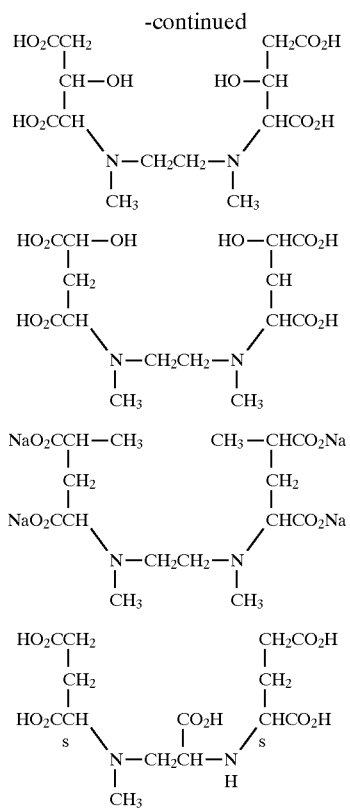

The compounds represented by the general formula (I) of the present invention can be synthesized by introducing a substituent on N of the compound represented by the general formula (A) as shown in scheme 1. On the contrary, they can be synthesized also by introducing succinic acid group into a diamine derivative (B) having the substituent as shown in scheme 2. The compounds of the general formula (I) can be synthesized by various other methods.

Scheme 1

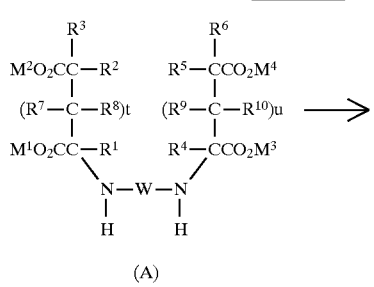

wherein $R^1$, $R^2$, $R^3$, $R^4$, $R^5$, $R^6$, $R^7$, $R^8$, $R^9$, $R^{10}$, W $X^1$, $X^2$, $M^1$, $M^2$, $M^3$ and $M^4$ are as defined in the general formula (I), preferred examples of them are also the same as those described above, and t and u each represent an integer of 0 to 5.

Scheme 2

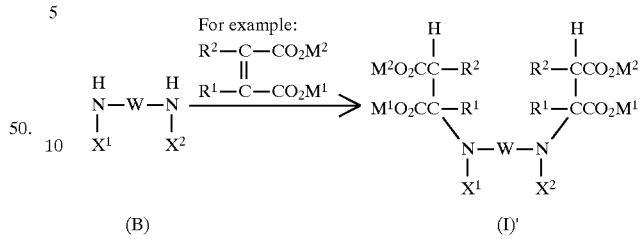

wherein $R^1$, $R^2$, W, $X^1$, $X^2$, $M^1$, $M^2$, $M^3$ and $M^4$ are as defined in the general formula (I), and preferred examples of them are also the same as those described above.

Various methods are known for introducing the substituent in the synthesis method of scheme 1. For example, the alkylation can be conducted by Leuckart reaction [Berichte, 18, 2341 (1885) and Journal of Organic Chemistry, 23, 1122 (1958)] or substitution reaction with a halogen compound ("Jikken Kagaku Koza", the 4th Edition, Vol. 20, pp. 284 to 288). The compounds of the general formula (A) in scheme 1 can be synthesized by a method described in J.P. KOKAI Nos. Sho 63-199295 and Hei 3-173857.

The synthesis method of scheme 2 can be conducted according to the description given in J.P. KOKAI Nos. Sho 63-199295 and Hei 3-173857 and U.S. Pat. No. 3,158,635.

When the Leuckart reaction is employed in the scheme 1, a solvent may be used. The solvent is not particularly limited so far as it does not participate in the reaction. The solvent is, for example, water, an alcohol (such as methanol or ethanol), acetonitrile, dimethylformamide or dimethylacetamide. Although the reaction proceeds even under an acidic condition, the reaction is preferably conducted under a neutral to alkaline condition. The bases include, for example, alkalis (such as sodium hydroxide and potassium hydroxide) and tertiary amines (such as triethylamine). The reaction is conducted usually at 0° to 190° C., preferably 10° to 100° C. and more preferably 20° to 90° C.

Furthermore, the method (synthesis of ethylenediamine-N,N'-disuccinic acid) described on pages 311 of "Chelate Kagaku (Chelate Chemistry)" (5) edited by Kagehei Ueno and published by Nanko-do can be used for reference. Namely, when the coordination group moieties which comprises carboxylic groups on N's of the diamine are the same each other, the process which comprises bonding the secondary amine derivatives (C) by the divalent bonding group having eliminating groups as shown in scheme 3 can be employed.

Scheme 3

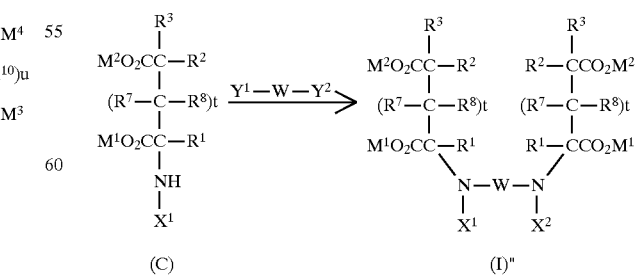

wherein $R^1$, $R^2$, $R^3$, $R^7$, $R^8$, W, $X^1$, $M^1$ and $M^2$ are as defined in the general formula (I), and t and u each represent an integer of 0 to 5. $Y^1$ and $Y^2$ each represent eliminating groups, for example, halogen atoms such as fluorine, chlorine, bromine or iodine; or sulfonate groups such as methylsulfonate or p-toluene sulfonate. The general formula (I)" represents compounds which are a part of the compounds having the general formula (I).

A typical synthesis example for the compounds of the general formula (I) of the present invention is given below.

SYNTHESIS EXAMPLE 1

Synthesis of compound 1

15 g (0.043 mol) of ethylenediaminedisuccinic acid and 15 ml of water were fed into a three-necked flask. pH of the obtained mixture was adjusted to 9 with 49% aqueous sodium hydroxide solution. 12 g (0.26 mol) of formic acid was dropped therein under cooling with an ice bath. pH of the obtained mixture was adjusted to 9 with 49% aqueous sodium hydroxide solution. 4.6 g (0.057 mol) of 37% formalin was dropped therein and the obtained mixture was heated to 90° C . 4.6 g (0.057 mol) of 37% formalin was dropped 7 times at intervals of 3 hours. After the completion of the dropping, the heating and stirring were continued for additional 5 hours. The reaction solution was cooled and pH thereof was adjusted to 1.5 with hydrochloric acid. The precipitates thus formed were taken by filtration, and the filtrate was desalted by electrodialysis. pH of the solution was adjusted to 1.5 again with hydrochloric acid, and the solution was concentrated under reduced pressure. After leaving the concentrate to stand in a refrigerator for 1 month, the intended compound 1 was obtained in the form of crystals. Yield: 8.5 g (61%).

Elementary analysis for $C_{12} H_{20} N_2 O_8 = 320.30$:

|  | H | C | N |
|---|---|---|---|
| calculated: | 6.26 | 45.00 | 8.75 |
| found: | 6.35 | 49.96 | 8.67 |

Other compounds can also be synthesized in the same manner as that described above.

The metal salts constituting the heavy metal chalate compound with the compounds of the general formula (I) of the present invention (hereinafter referred to as "heavy metal chelate compound of the present invention") include Fe (III) (such as ferric sulfate, ferric chloride, feric nitrate, ferric sulfate and ferric phosphate) and also Mn (III), Co (III), Rh (II), Th (III), Au (II), Au (III) and Ce (IV). Among them, Fe (III) and Co (III) are preferred. Fe (III) is particularly preferred.

The heavy metal chelate compound of the present invention may either the heavy metal chelate compound itself or a combination of a compound of the above general formula (I) and the above-described metal salt to be reacted together in the solution. Also, ammonium salt or alkali metal salt (such as lithium, sodium or potassium salt) of the compound of the general formula (I) may be reacted with the metal salt in the solution to form the heavy metal chelate compound to be used.

The compound of the general formula (I) is used in such an amount that the molar ratio thereof to the metal ion is at least 1.0. The molar ratio is preferably high when the stability of the metal chelate compound is low. It is usually in the range of 1 to 30.

The compound of the general formula (I) of the present invention may be incorporated into a photosensitive material (for example, a photo constituent layer such as photographic emulsion layer or intermediate layer), as an additive for a silver halide photograph which exerts no bad influence on the photographic characteristics (such as sensitivity and fog); or it may be incorporated into a processing composition for the photography.

By using the above-described compound, the effects of the chelating agent, bleaching agent, oxidizing agent, suspending agent, antistaining agent, stabilizer and reducing agent can be obtained.

The heavy metal chelate compound of the present invention is effective in oxidizing silver halide photosensitive materials (particularly in bleaching color photosensitive materials).

In a preferred embodiment of the processing composition containing the heavy metal chelate compound of the present invention, the developed silver could be rapidly bleached by processing the imagewise-exposed silver halide color photographic sensitive material with a processing solution having a bleaching function and containing at least the heavy metal chelating compound of the present invention as the bleaching agent after the color development. In addition, the formation of a precipitate, staining of the surface of the photosensitive material and clogging of the filter caused by conventional bleaching agents usable for the rapid bleaching in the running process are only slight.

The present invention is characterized by the bleaching agent particularly in a processing composition having the bleaching function, usable as the oxidizing agent in the photographic processing composition. Other conditions such as the material can be suitably selected from ordinary materials, etc.

The description will be made on the processing composition (processing solution) containing the heavy metal chelate compound and chelating agent of the present invention. The form of the composition is not limited to the liquid but it may be in the form of a solid (such as powder, granules) or paste.

The heavy metal chelate compound or the chelating agent of the present invention may be contained in any types of processing solution (such as bleach-fixing solution, fixing solution, intermediate bath used between the color development and desilvering step or stabilizer). The heavy metal chelate compound is usually used as a bleaching agent or a reducing agent. Therefore, bleachig solution (composition) comprising the heavy metal chelate compound or bleach-fixing solution (composition) comprising the compound and a fixing agent is used as photographic processing solution. The chelating agent can be added to developing solution such as color developing solution, fixing solution, bleaching solution, beach-fixing solution, stabilizing solution or washing water. When the processing solution contains 0.005 to 1 mol of the heavy metal chelate compound per liter thereof, the solution is particularly effective as a reducing solution for black-and-white photosensitive materials or as a solution (bleaching solution or bleach-fixing solution) having a function of bleaching color photosensitive materials.

The description will be made on a preferred embodiment of the processing solution having the bleaching function. When 0.005 to 1 mol as described above, preferably 0.01 to 0.5 mol, and particularly preferably 0.05 to 0.5 mol, of the heavy metal chelate compound of the present invention is contained in 1l of the processing solution having the bleaching function, the solution is effective as the bleaching agent. The heavy metal chelate compound of the present invention is capable of exhibiting its excellent effect even when its concentration is as low as 0.005 to 0.2 mol, preferably 0.01 to 0.2 mol and more preferably 0.05 to 0.18 mol per liter of the processing solution.

When the heavy metal chelate compound is to be added to a processing solution having the bleaching function, it can be used not only in an oxidized form [such as a chelate compound of Fe (III)] but also in a reduced form [such as a chelate compound of Fe (II)].

When the heavy metal chelate compound of the present invention is used as a bleaching agent in a processing solution having the bleaching function, it may be used in combination with another bleaching agent so far as the effect of the present invention can be obtained (the amount of the other bleaching agent is preferably not more than 0.01 mol, more preferably not more than 0.005 mol per liter of the processing solution). The bleaching agents include compounds of polyvalent metals such as iron (III), peracids, quinones and nitro compounds. Typical bleaching agents include iron (III) complex salts of organic compounds such as iron complex salts of ethylenediaminetetraacetic acid, diethylenetriaminepentaacetic acid, cyclohexanediaminetetraacetic acid, methyliminodiacetic acid and glycol ether diaminetetraacetic acid, and bleaching agents typified by iron complex salts of 1,3-propanediaminetetraacetic acid and the like described from right, lower column on p. 4 to left upper column on p. 5 of J. P. KOKAI No. Hei 4-121739; carbamoyl bleaching agents described in J.P. KOKAI No. Hei 4-73647; bleaching agents having a heterocyclic ring described in J.P. KOKAI No. Hei 4-174432; bleaching agents described in European Patent Publication No. 520457 and typified by iron (III) complex salts of N-(2-carboxyphenyl)iminodiacetic acid; bleaching agents described in European Patent Publication No. 530828A1 and typified by ethylenediaminne-N-2-carboxyphenyl-N,N', N'-triacetate ferric acetate; bleaching agents described in European Patent Publication No. 501479; bleaching agents described in European Patent Publication No. 567126; bleaching agents described in European Patent Publication No. 127145; and ferric aminopolycarboxylates and salts of them described on page (11) of J.P. KOKAI No. Hei 3-144446. These examples by no means limit the bleaching agents usable in combination with the heavy metal chelate compounds of the present invention.

The processing solution containing the heavy metal chelate compound of the present invention and having the bleaching function preferably contains a halide such as a chloride, bromide or iodide as a rehalogenating agent for accelerating the oxidation of silver in addition to the metal chelate compound as the bleaching agent. Also an organic ligand capable of forming a difficultly soluble silver salt may be added in place of the halide. The halide is added in the form of an alkali metal salt, ammonium salt, guanidine salt or amine salt. Examples of them include sodium bromide, ammonium bromide, potassium chloride, guanidine hydrochloride, potassium bromide and potassium chloride. The amount of the rehalogenating agent in the processing solution having the bleaching function of the present invention is 2 mol/l or smaller. The amount thereof in the bleaching solution is preferably 0.01 to 2.0 mol/l, more preferably 0.1 to 1.7 mol/l and particularly preferably 0.1 to 0.6 mol/l. The amount thereof in the bleach-fixing solution is preferably 0.001 to 2.0 mol/l, more preferably 0.001 to 1.0 mol/l and particularly preferably 0.001 to 0.5 mol/l.

The bleaching solution or bleach-fixing solution according to the present invention further contains, if necessary, a bleach-accelerating agent, anti-corrosive for protecting the processing bath tank from corrosion, buffer for keeping pH of the solution, fluorescent brightening agent, antifoaming agent, etc.

The bleaching accelerators usable herein include, for example, mercapto group or disulfido group-containing compounds described in U.S. Pat. No. 3,893,858, German Patent No. 1,290,821, British Patent No. 1,138,842, J.P. KOKAI No. Sho 53-95630 and Research Disclosure No. 17129 (July, 1978); thiazolidine derivatives described in J.P. KOKAI No. Sho 50-140129; thiourea derivatives described in U.S. Pat. No. 3,706,561; iodides described in J.P. KOKAI No. Sho 58-16235; polyethylene oxides described in German Patent No. 2,748,430; and polyamine compounds described in J.P. KOKOKU No. Sho 45-8836. Further, compounds described in U.S. Pat. No. 4,552,834 are also preferred. These bleaching accelerators may be added to the photosensitive material. These bleaching accelerators are particularly effective when a color photosensitive material for photography is to be bleach-fixed. Mercapto compounds described in British Patent No. 1,138,842 and J.P. KOKAI No. Hei 2-190856 are particularly preferred.

The bleaching solution or bleach-fixing solution of the present invention has a pH of 2.0 to 8.0, preferably 3.0 to 7.5. When the photographic sensitive material is to be bleached or bleach-fixed immediately after the color development, pH of the solution is controlled preferably at 7.0 or below, more preferably 6.4 or below for inhibiting the bleach fog. pH of the bleaching solution is particularly preferably 3.0 to 5.0. When pH is 2.0 or below, the metal chalate of the invention tends to be unstable. Preferred pH range is thus 2.0 to 6.4. For color printing materials, pH is preferably in the range of 3 to 7.

pH buffering agent used for this purpose is not particularly limited so far as it is not easily oxidized and it has the buffering effect in the above-described pH range. The pH buffering agents include organic acids such as acetic acid, glycolic acid, lactic acid, propionic acid, butyric acid, malic acid, chloroacetic acid, levulinic acid, ureidopropionic acid, formic acid, pyruvic acid, isobutyric acid, pivalic acid, aminobutyric acid, valeric acid, isovaleric acid, asparagine, alanine, arginine, ethionine, glycine, glutamine, cysteine, serine, methionine, leucine, histidine, benzoic acid, hydroxybenzoic acid, nicotinic acid, oxalic acid, malonic acid, succinic acid, tartaric acid, maleic acid, fumaric acid, oxalo acid, glutaric acid, adipic acid, aspartic acid, glutamic acid, cystine, ascorbic acid, phthalic acid and terephthalic acid; and organic bases such as pyridine, dimethylpyrazole, 2-methyl-o-oxazoline, aminoacetonitrile and imidazole. A combination of two or more of these buffering agents may also be used. Organic acids having an acid dissociation constant (pKa) of 2.0 to 5.5 are preferred and dibasic acids are more preferred in the present invention.

Particularly preferred dibasic acids include succinic, glutaric, maleic, fumaric, malonic and adipic acids. Succinic, glutaric and maleic acids are the most preferred. These organic acids are usable also in the forms of alkali metal salts (such as lithium, sodium and potassium salts) and ammonium salts thereof. The amount of the buffering agent used is desirably not larger than 3.0 mol, preferably 0.1 to 2.0 mol, more preferably 0.2 to 1.8 mol, and particularly 0.4 to 1.5 mol, per liter of the processing solution having the bleaching function.

pH of the processing solution having the bleaching function may be controlled in the above-described range by using a combination of the above-described acid with an alkali (such as ammonia water, KOH, NaOH, potassium carbonate, sodium carbonate, imidazole, monoethanolamine or diethanolamine). Among them, ammonia water, KOH, NaOH, potassium carbonate and sodium carbonate are preferred.

The anti-corrosive is preferably a nitrate such as ammonium nitrate, sodium nitrate or potassium nitrate. It is used in an amount of 0.01 to 2.0 mol/l, preferably 0.05 to 0.5 mol/l.

As the recognition of the global environmental safeguard is being improved recently, efforts are made for reducing the amount of nitrogen atom discharged into the environment. From this viewpoint, it is desirable that also the processing solution of the present invention is substantially free from ammonium ion.

The expression "substantially free from ammonium ion" herein indicates that ammonium ion concentration is not higher than 0.1 mol/l, preferably not higher than 0.08 mol/l, and more preferably not higher than 0.01 mol/l. Particularly preferably no ammonium is contained therein.

Cations usable instead of ammonium ion in order to reduce the ammonium ion concentration into the range of the present invention are preferably alkali metal ions and alkaline earth metal ions. Among them, the alkali metal ions are preferred. Particularly, lithium, sodium and potassium ions are preferred. Specifically, they include sodium and potassium salts of ferric complexes of organic acids as a bleaching agents; potassium bromide and sodium bromide as a rehalogenating agent in the processing solution having the bleaching function; and potassium nitrate and sodium nitrate.

The alkalis used for controlling pH are preferably potassium hydroxide, sodium hydroxide, potassium carbonate and sodium carbonate.

It is particularly preferred to use the processing solution of the present invention having the bleaching function under aeration so as to keep the photographic properties very stable. The aeration can be conducted by a technique well-known in the art, such as the introduction of air into the processing solution having the bleaching function or absorption of air with an ejector.

In the introduction of air, it is preferred to release air into the solution with an air-diffusing pipe having fine pores. Such an air-diffusing pipe is widely used for an aeration tank in the treatment of activated sludge. For the aeration, the data described in Z-121, Using Process C-41, the 3rd Edition (1982), pp. BL-1 to BL-2 (published by Eastman Kodak Co.) can be employed. In a step wherein the processing solution of the present invention having the bleaching function is used, the strong stirring is preferred. The contents of J.P. KOKAI No. Hei 3-33847 (from line 6, right upper column to line 2, left lower column, page 8) can be directly employed.

The bleaching or bleach-fixing can be conducted in the temperature range of 30° to 60° C., preferably 35° to 50° C.

The time necessitated for the bleaching and/or bleach-fixing step for photographic sensitive materials is in the range of 10 seconds to 7 minutes, preferably 10 seconds to 4 minutes. The time for photosensitive materials for prints is 5 to 70 seconds, preferably 5 to 60 seconds and more preferably 10 to 45 seconds. Under these preferred processing conditions, excellent results were rapidly obtained without increase of stains.

The photosensitive material processed with the processing solution having the bleaching function is then fixed or bleach-fixed. When the processing solution having the bleaching function is a bleach-fixing solution, the material may be fixed or bleach-fixed, if necessary, thereafter. The fixing solutions or bleach-fixing solutions are preferably those described from line 16, right lower column, page 6, to line 15, left upper column, page 8 of also J.P. KOKAI No. Hei 3-33847.

Although ammonium thiosulfate has been usually used as the fixing agent in the desilvering step, other well-known fixing agents such as meso-ionic compounds, thioether compounds, thioureas, a large amount of iodides or hypo are also usable. These compounds are described in J.P. KOKAI Nos. Sho 60-61749, Sho 60-147735, Sho 64-21444,, Hei 1-201659, Hei 1-210951 and Hei 2-44355, and U.S. Pat. No. 4,378,424. The fixing agents are, for example, ammonium thiosulfate, sodium thiosulfate, potassium thiosulfate, guanidine thiosulfate, ammonium thiocyanate, sodium thiocyanate, potassium thiocyanate, dihydroxyethyl thioether, 3,6-dithia-1,8-octanediol and imidazle. Among them, the thiosulfates and meso-ionic compounds are preferred. Although ammonium thiosulfate is preferred from the viewpoint of the rapid fixing, sodium thiosulfate and mesoionic compounds are more preferred from the viewpoint of protecting the environment by using a substantially ammonium ion-free processing solution. The fixing can be conducted more rapidly by using a combination of two or more kinds of fixing agents. For example, ammonium thiosulfate or sodium thiosulfate is preferably used in combination with the above-described ammonium thiocyanate, imidazole, thiourea, thioether, etc. In such a case, the latter fixing agent is used preferably in an amount of 0.01 to 100 molar % based on ammonium thiosulfate or sodium thiosulfate.

The amount of the fixing agent is 0.1 to 3.0 mol, preferably 0.5 to 2.0 mol, per liter of the bleach-fixing solution or fixing solution. pH of the fixing solution which varies depending on the variety of the fixing agent is usually in the range of 3.0 to 9.0. Particularly when a thiosulfate is used, pH of the fixing solution is preferably 5.8 to 8.0 for obtaining a stable fixing function.

A preservative can be added to the bleach-fixing solution or fixing solution to improve the stability with time of the solution. When the bleach-fixing solution or fixing solution contains a thiosulfate, the effective preservatives are sulfites and/or hydroxylamines, hydrazine and bisulfite adducts of aldehydes (such as bisulfite adduct of acetaldehyde and particularly preferably bisulfite adducts of aromatic aldehydes described in J.P. KOKAI Hei 1-298935).

The bleach-fixing solution containing the heavy metal chelate compound of the present invention preferably contains at least one selected from sulfinic acids and salts thereof. Preferred examples of sulfinic acids and salts thereof are compounds described in J.P. KOKAI Nos. Hei 1-230039, 1-224762, 1-231051, 1-271748, 2-91643, 2-251954, 2-252955, 3-55542, 3-158848, 4-51237 and 4-329539, U.S. Pat. Nos. 5,108,876 and 4,939,072, and EP Nos. 255722A and 463639. Substituted or unsubstituted arylsulfinic acids and salts thereof are more preferred, and substituted or unsubstituted phenylsulfinic acids and salts thereof are particularly preferred. The substituents include, for example, alkyl groups having 1 to 4 carbon atoms, aryl groups having 6 to 10 carbon atoms, carbamoyl groups having 1 to 5 carbon atoms, alkoxycarbonyl groups having 1 to 5 carbon atoms, alkoxyl groups having 1 to 4 carbon atoms, sulfinic acid groups, sulfonic acid groups, carboxylic acid groups, hydroxyl groups and halogen atoms.

Preferred examples of the sulfinic acids and salts thereof are given below, which by no means limit the present invention:

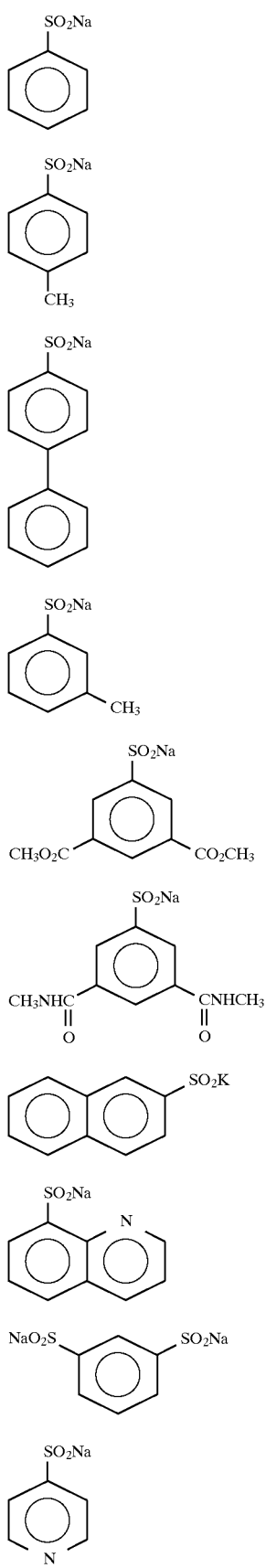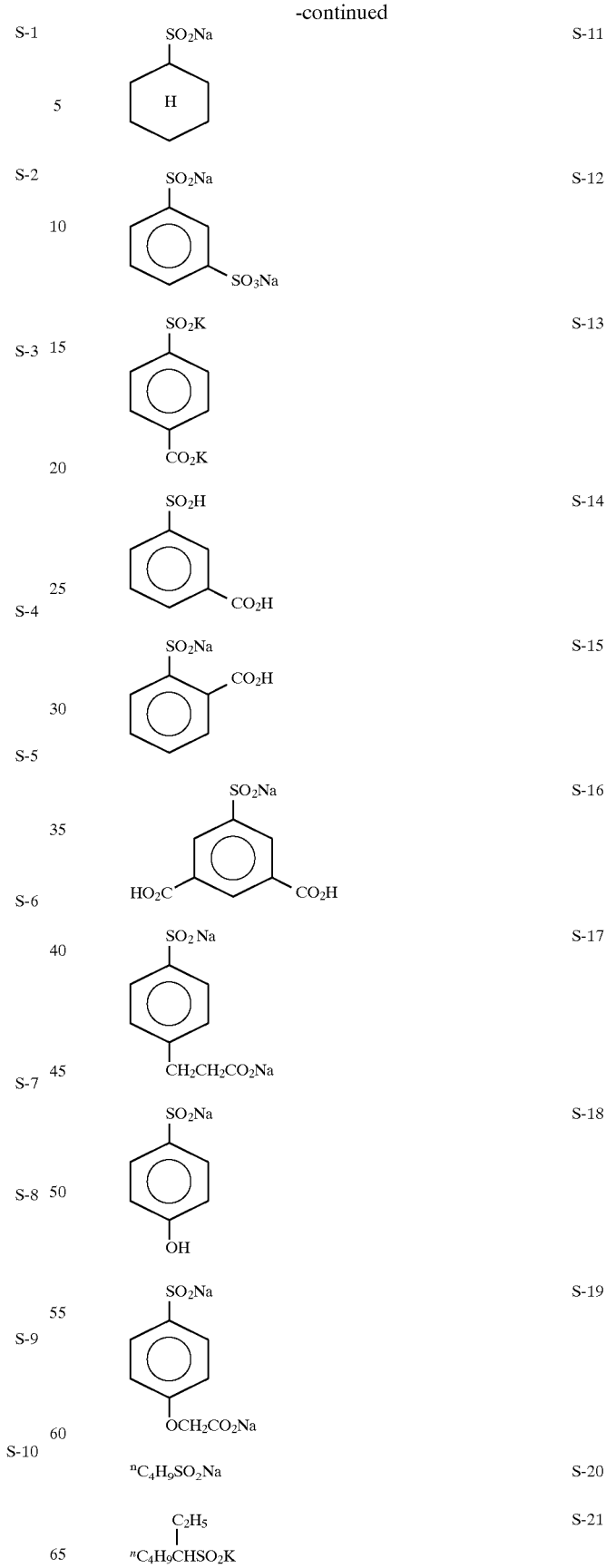

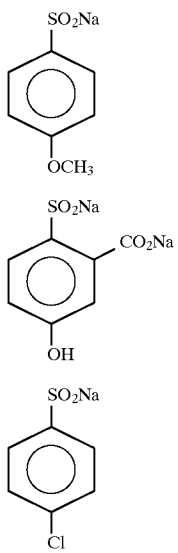

The amount of the sulfinic acids and salts thereof to be added to the bleach-fixing solution or fixing solution is $1\times10^{-4}$ to 1 mol, preferably $1\times10^{-3}$ to 0.1 mol and more preferably $1\times10^{-2}$ to 0.1 mol per liter of processing solution.

A buffering agent is preferably added to the bleach-fixing solution or fixing solution in order to keep pH of the solution constant. The buffering agents include, for example, phosphates; imidazoles such as imidazole, 1-methylimidazole, 2-methylimidazole and 1-ethylimidazole; triethanolamine, N-allylmorpholines and N-benzoylpiperazine.

By adding various chelating agents to the fixing solution, iron ion brought thereinto from the bleaching solution can be masked to improve the stability of the solution. Examples of the preferred chelating agents include, in addition to the compounds of the present invention, 1-hydroxyethylidene-1,1-diphosphonic acid, n itritotrimethylenephosphonic acid, 2-hydroxy-1,3-diamino propanetetraacetic acid, ethylenediaminetetraacetic acid, diethylenetriaminepentaacetic acid, ethylenediamine-N-( β-hydroxyethyl) -N,N',N'-triacetic acid, 1,2-diaminopropanetetraacetic acid, 1,3-diaminopropanetetraacetic acid, nitrilotriacetic acid, cyclohexanediaminetetraacetic acid, iminodiacetic acid, dihydroxyethylglycine, ethyl ether diaminetetraacetic acid, glycol ether diaminetetraacetic acid, ethylenediaminetetrapropionic acid, phenylenediaminetetraacetic acid, 1,3-diaminopropanol-N,N,N',N'-tetramethylenephosphonic acid, ethylenediamine-N,N,N',N'-tetramethylenephosphonic acid, 1,3-propylenediamine-N,N,N',N'-tetramethylenephosphonic acid, serine-N,N-diacetic acid, 2-methylserine--N,N-diacetic acid, 2-hydroxymethylserine-N,N-diacetic acid, hydroxyethyliminodiacetic acid, methyliminodiacetic acid, N-(2-acetamido)-iminodiacetic acid, nitrilotripropionic acid, ethylenediaminediacetic acid, ethylenediaminedipropionic acid, 1,4-diaminobutanetetraacetic acid, 2-methyl-1,3-diaminopropanetetraacetic acid, 2-dimethyl-1,3-diaminopropanetetraacetic acid, alanine, tartaric acid, hydrazidodiacetic acid, N-hydroxyiminodipropionic acid, and alklai metal salts (such as lithium, sodium and potassium salts) thereof and ammonium salts thereof.

The process in the fixing step can be conducted at 30° to 60° C., and the temperature is preferably 35° to 50° C.

The time necessitated for the fixing step is 15 seconds to 2 minutes, preferably 25 seconds to 1 minute 40 seconds for the photosensitive materials for photography, and 8 to 80 seconds, preferably 10 to 45 seconds for the photosensitive materials for printing.

The desilvering step usually comprises the combination of bleaching step, bleach-fixing step and fixing step. Examples of them are as follows:

(1) bleaching/fixing
(2) bleaching/bleach-fixing
(3) bleaching/bleach-fixing/fixing
(4) bleaching/washing with water/fixing
(5) bleach-fixing
(6) fixing/bleach-fixing.

For the photosensitive materials for photography, (1), (2), (3), (4) and (5) are preferred. In the present invention, the remarkable effects are obtained in the steps including bleach-fixing such as (2), (3) and (5); and step (5) is particularly preferred.

The present invention can be employed also in a desilvering process which comprises the process in control bath, stop bath, water washing bath, etc., after the color development process.

The processing solution having bleaching function of the present invention is reusable by recovering the overflow used in the process and adding the ingredients thereof to regulate the composition thereof. The present invention is also suitable for this process usually called "regeneration". The details of the regeneration are described on pages 39 to 40 of Fuji Film Processing Manual, Fuji Color Negative Film, CN-16 Process (revised in August, 1990) published by Fuji Photo Film Co., Ltd.

Although the kit for preparing the processing solution of the present invention having the bleaching effect may be in the form of either liquid, powder or solid, the powder is more easily prepared, since most starting materials except for ammonium salts are in powder form having only a slight hygroscopicity.

Further, the kit for the regeneration is preferably in the form of a powder from the viewpoint of reduction in the quantity of waste water, since it can be directly added without using excess water.

For the regeneration of the processing solution having the bleaching function, a method described in "Shashin Kogaku no Kiso, — Gin'en Shashin Hen— (The Fundamentals of Photographic Engineering, —Edition of Silver Salt Photographs—)" (edited by Nihon Shashin Gakkai and published by Corona in 1979) can be employed in addition to the above-described aeration method. Specifically, the bleaching solution can be regenerated by an electrolytic regeneration method or a method wherein bromic acid, chlorous acid, bromine, a bromine precursor, a persulfate, or hydrogen peroxide, or a combination of a catalyst with hydrogen peroxide, bromous acid or ozone is used.

In the electrolytic regeneration method, a cathode and an anode are placed in the same bleaching bath, or the anodic bath is separated from the cathodic bath with a diaphragm. In another electrolytic regeneration method, the bleaching solution and developer and/or fixing solution can be regenerated at the same time by using a diaphragm.

The fixing solution and bleach-fixing solution are regenerated by electrolytically reducing silver ion accumulated therein. To maintain the fixing function, it is also preferred to remove the accumulated halogen ion with an anion exchange resin.

For reducing the quantity of the washing water, ion-exchange or ultrafiltration is employed. The ultrafiltration is particularly preferred.

The present invention is useful also for preparing a reducing solution for retouching a silver image comprising halftone dots and/or lines obtained by exposing and then developing a silver halide photosensitive material for reprophotography.

The chelating agent of the general formula (I) and heavy metal chelate compound thereof are useful for every sort of processing compositions used for processing silver halide black-and-white photosensitive materials and silver halide color photosensitive materials. Those used for processing the silver halide black-and-white photosensitive materials include, for example, general black-and-white developer, contagious developer for lith films, fixing solution and washing water. Those used for processing the silver halide color photosensitive materials include, for example, color developer, bleaching solution, fixing solution, bleach-fixing solution, control bath, stop bath, hardening solution, washing water, stabilizer, rinsing solution, fogging solution and toning solution. The uses of the chelating agent of the general formula (I) and heavy metal chelate compound thereof are not limited to those described above. These compounds of the present invention are effective particularly for the black-and-white developer, color developer, fixing solution and stabilizing solution. They are particularly recommended for the black-and-white developer and color developer.

The amount of the compound of the general formula (I), which varies depending on the processing composition, to which the compound is added, is usually in the range of 10 mg to 50 g per liter of the composition.

In particular, when the compound is added to the black-and-white developer or color developer, the amount thereof is preferably 0.5 to 10 g per liter of the processing solution. When it is added to a bleaching solution (comprising, for example, hydrogen peroxide, persulfuric acid, bromic acid or the like), the amount thereof is 0.1 to 20 g; when it it added to a fixing solution or bleach-fixing solution, the amount thereof is 1 to 40 g; and when it is added to a stabilizing bath, the amount thereof is 50 mg to 1 g, per liter of the processing solution, respectively.

The compounds of the general formula (I) may be used either singly or in combination of two or more of them.

When the compound of the present invention is added to the color developer or black-and-white developer, the precipitation is inhibited and the stability of the developer is improved.

The color developers usable in the present invention include those described from line 6, left, upper column, page 9 to line 6, right, lower column, page 11 of J.P. KOKAI No. Hei 3-33847 and those described in J.P. KOKAI No. Hei 5-197107.

As the color developing agent used in the color development step, known aromatic primary amine color developing agents are usable. p-Phenylenediamine compounds are preferably used. Typical examples of them include 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-β-methoxyethylaniline, 4-amino-3-methyl-N-methyl-N-(3-hydroxypropyl) aniline, 4-amino-3-methyl-N-ethyl-N-(3-hydroxypropyl)aniline, 4-amino-3-methyl-N-ethyl-N-(2-hydroxypropyl)aniline, 4-amino-3-ethyl-N-ethyl-N-(3-hydroxypropyl)aniline, 4-amino-3-methyl-N-propyl-N-(3-hydroxypropyl) aniline, 4-amino-3-propyl-N-methyl-N-(3-hydroxypropyl)aniline, 4-amino-3-methyl-N-methyl-N-(4-hydroxybutyl)aniline, 4-amino-3-methyl-N-ethyl-N-(4-hydroxybutyl)aniline, 4-amino-3-methyl-N-propyl-N-(4-hydroxybutyl) aniline, 4-amino-3-ethyl-N-ethyl-N-(3-hydroxy-2-methylpropyl)aniline, 4-amino-3-methyl-N,N-bis(4-hydroxybutyl)aniline, 4-amino-3-methyl-N,N-bis(5-hydroxypentyl)aniline, 4-amino-3-methyl-N-(5-hydroxypentyl)-N-(4-hydroxybutyl)aniline, 4-amino-3-methoxy-N-ethyl-N-(4-hydroxybutyl) aniline, 4-amino-3-ethoxy-N,N-bis(5-hydroxypentyl)aniline, 4-amino-3-propyl-N-(4-hydroxybutyl)aniline and sulfates, hydrochlorides and p-toluenesulfonates of them. Among them, particularly preferred compounds are 3-methyl-4-amino-N-ethyl-N-β-hydroxyethylaniline, 4-amino-3-methyl-N-ethyl-N-(3-hydroxypropyl)aniline, 4-amino-3-methyl-N-ethyl-N-(4-hydroxybutyl)aniline and hydrochlorides, p-toluenesulfonates and sulfates of them. A combination of two or more of these compounds are usable depending on the purpose.

Color developing agents described in European Patent Publication No. 410450 and J.P. KOKAI No. Hei 4-11255 are also preferred.

These p-phenylenediamine derivatives may be in the form of salts thereof such as sulfates, hydrochlorides, sulfites, naphthalenedisulonates and p-toluenesulfonates. The amount of the aromatic primary amine developing agent used is preferably 0.0002 to 0.2 mol, more preferably 0.001 to 0.1 mol, per liter of the color developer.

The temperature for the process with the color developer is 20 to 55° C., preferably 30° to 55° C., in the present invention. The process time ranges from 20 seconds to 5 minutes, preferably from 30 seconds to 3 minutes 20 seconds and more preferably from 1 minute to 2 minutes 30 seconds for the photographic sensitive materials. The process time ranges from 10 seconds to 1 minute 20 seconds, preferably 10 to 60 seconds and more preferably 10 to 40 seconds for the materials for prints.

If necessary, a preservative may be added to the color developer. The preservatives include sulfites such as sodium sulfite, potassium sulfite, sodium bisulfite, potassium bisulfite, sodium metasulfite and potassium metasulfite, and carbonyl/sulfuric acid adduct.

It is preferred that the color developer contains a compound for directly preserving the above-described aromatic primary amine color developing agent, which is for example hydroxylamines such as compounds described in J.P. KOKAI Nos. Sho 63-5341 and Sho 63-106655, particularly those having sulfo and carboxyl groups, hydroxamic acids described in J. P. KOKAI No. Sho 63-43138, hydrazines and hydrazides described in J.P.

KOKAI No. Sho 63-146041, phenols described in J.P. KOKAI Nos. Sho 63-44657 and Sho 63-58443, α-hydroxyketones and α-aminoketones described in J.P. KOKAI No. Sho 63-44656, and/or saccharides described in J.P. KOKAI No. Sho 63-36244. Such a compound can be used in combination with monoamines described in J.P. KOKAI Nos. Sho 63-4235, 63-24254, 63-21647, 63-146040, 63-27841 and 63-25654, diamines described in J.P. KOKAI Nos. Sho 63-30845, 63-14640 and 63-43139, polyamines described in J.P. KOKAI Nos. Sho 63-21647, 63-26655 and 63-44655, nitroxy radicals described in J.P. KOKAI No. Sho 63-53551, alcohols described in J.P. KOKAI Nos. Sho 63-43140 and 63-53549, oximes described in J.P. KOKAI No. Sho 63-56654 and tertiary amines described in J.P. KOKAI No. Sho 63-239447.

The color developer may contain, if necessary, also a preservative such as metals described in J.P. KOKAI Nos. Sho 57-44148 and 57-53749, salicylic acids described in J.P. KOKAI No. Sho 59-180588, alkanolamines described in J.P. KOKAI No. Sho 54-3582, polyethyleneimines described in J.P. KOKAI No. Sho 56-94349 and aromatic polyhydroxy compounds described in U.S. Pat. No. 3,746,544. Particularly, the aromatic polyhydroxy compounds are preferred. Such a preservative is used in an amount of 0.005 to 0.2 mol, preferably 0.01 to 0.05 mol, per liter of the color developer.

The color developer is usable in the pH range of 9 to 12, preferably 9.5 to 11.5 in the present invention. The color developer may further contain known compounds used as the ingredients of developers. Buffers are preferably used for keeping pH in the above-described range.

Examples of the buffers include sodium carbonate, potassium carbonate, sodium hydrogencarbonate, potassium hydrogencarbonate, trisodium phosphate, tripotassium phosphate, disodium phosphate, dipostassium phosphate, sodium borate, potassium borate, sodium tetraborate (borax), potassium tetrabroate, sodium o-hydroxybenzoate (sodium salicylate), potassium o-hydroxybenzoate, sodium 5-sulfo-2-hydroxybenzoate (sodium 5-sulfosalicylate) and potassium 5-sulfo-2-hydroxybenzoate (potassium 5-sulfosalicylate). However, the buffers usable in the present invention are not limited to those listed above. The amount of the buffer to be added to the color developer is preferably at least 0.1 mol/l, particularly preferably 0.1 to 0.4 mol/l.

In the present invention, various chelating agents are usable so far as they do not impair the effect of the compounds of the present invention.

The chelating agents are preferably organic acid compounds such as aminopolycarboxylic acids, organic phosphonic acids and phosphonocarboxylic acids. They are typified by nitrilotriacetic acid, diethylenetriaminepentaacetic acid, ethylenediaminetetraacetic acid, N,N,N-trimethylnephosphonic acid, ethylenediamine-N,N,N',N'-tetramethylenephosphonic acid, transcyclohexanediamine-tetraacetic acid, 1,2-diaminopropanetetraacetic acid, hydroxyethyliminodiacetic acid, glycol etherdiaminetetraacetic acid, ethylenediaminebis-o-hydroxyphenylacetic acid, 2-phosphonobutane-1,2,4-tricarboxylic acid, 1-hydroxyethylidene-1,1-diphosphonic acid and N,N'-bis(2-hydroxybenzyl) ethylenediamine-N,N'-diacetic acid. These chelating agents are used in an amount of, for example, 0.0001 to 0.05 mol, per liter of the processing solution.

The color developer of the present invention may contain, if necessary, a development accelerator.

The development accelerators include thioether compounds described in J. P. KOKOKU Nos. Sho 37-16088, 37-5987, 38-7826, 44-12380 and 45-9019 and U.S. Pat. No. 3,818,247; p-phenylenediamine compounds described n J. P. KOKAI Nos. Sho 52-49829 and 50-15554; quaternary ammonium salts described in J. P. KOKAI No. Sho 50-137726, J. P. KOKOKU No. Sho 44-30074 and J. P. KOKAI Nos. Sho 56-156826 and 52-43429; amine compounds described in U.S. Pat. Nos. 2,494,903, 3,128,182, 4,230,796 and 3,253,919, J. P. KOKOKU No. Sho 41-11431 and U.S. Pat. Nos. 2,482,546, 2,496,926 and 3,582,346; polyalkylene oxides described in J. P. KOKOKU Nos. Sho 37-16088 and 42-25201, U.S. Pat. No. 3,128,183, J. P. KOKOKU Nos. Sho 41-11431 and 42-23883 and U.S. Pat. No. 3,532,501; as well as imidazoles such as 2-methylimidazole and imidazole.

The addition of a 1-phenyl-3-pyrazolidone compound as an assistant developing agent is also preferred for the rapid development.

An antifoggant can be added, if necessary, to the color developer. The antifoggants usable herein include alkali metal halides such as sodium chloride, potassium bromide and potassium iodide and organic antifoggants. Typical examples of the organic antifoggants include nitrogen-containing heterocyclic compounds such as benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole, indazole, hydroxyazaindolizine and adenine.

The color developer may contain a fluorescent brightening agent which is preferably a 4,4'-diamino-2,2'-disulfostilbene compound. The amount of this agent added is 0 to 5 g/l, preferably 0.1 to 4 g/l.

If necessary, various surfactants such as an alkylsulfonic acid, arylsulfonic acid, aliphatic carboxylic acid or aromatic carboxylic acid may be added to the color developer.

Various known additives usually used in the art can be added to the black-and-white first developer used for the color reverse process and black-and-white developer for the black-and-white silver halide photosensitive material in which the compound of the present invention is usable.

Typical additives include developing agents such as 1-phenyl-3-pyrazolidone, Metol and hydroquinone; preservatives such as sulfites; accelerators comprising an alkali such as sodium hydroxide, sodium carbonate or potassium carbonate; inorganic or organic restrainers such as potassium bromide, 2-methylbenzimidazole and methylbenzothiazole; softening agents for hard water such as polyphosphates; and development restrainers such as a very small amount of iodides and mercapto compounds.

The bleaching solution, in which the compound of the present invention is usable, contains at least an oxidizing agent for oxidizing silver and a rehalogenating agent (or an organic ligand instead). The bleaching agents include known iron (III) complex salts of polyaminocarboxylic acids, hydrogen peroxide, persulfates, bromates, etc. A combination of two or more of them is also usable. The bleaching agent is used in an amount of 0.05 to 2 moles, preferably 0.1 to 5 moles, per liter of the bleaching solution. The rehalogenating agents are usually halides such as chlorides, bromides and iodides. Organic ligands capable of forming difficultly soluble silver salts are also usable in place of the halides. The amount of them is 0.1 to 2 mol/l, preferably 0.3 to 1.5 mol/l.

The halides are added in the form of alkali metal halides, ammonium halides, guanidine halides or amine halides. Specifically, they are sodium bromide, ammonium bromide, potassium chloride, guanidine hydrochloride, etc. Ammonium bromide is preferred.

The storability of the bleaching solution is improved when the compound of the present invention is added thereto. This effect is remarkable when the bleaching agent is hydrogen peroxide, a persulfate or a bromate.

The bleach-fixing solution to which the compound of the present invention can be added contains a fixing agent which will be described below, in addition to the bleaching agent, and, if necessary, the above-described rehalogenating agent. The amount of the bleaching agent in the bleach-fixing solution is equal to that in the bleaching solution. The amount of the rehalogenating agent is 0 to 2.0 mol/l, preferably 0.01 to 1.0 mol/l.

By adding the compound of the present invention to the bleach-fixing solution, the storability of the solution is improved.

The bleaching solution or bleach-fixing solution of the present invention may further contain, if necessary, a bleaching accelerator, an anticorrosive for protecting the processing bath from corrosion, a buffer for keeping pH of the solution, a fluorescent brightener, defoaming agent, etc. The conditions of the preferred bleaching solution, bleach-fixing solution and fixing solution of the present invention are the same as those described above for the processing solution which may contain the metal chelate compound of the present invention.

In the fixing solution of the present invention to which the compound of the general formula (I) is incorporated and, therefore, the storability of the solution is improved and also iron ion brought from the bleaching solution is masked to improve the stability of the solution.

The effects equal to those described above can be obtained also when the compound of the present invention is added to washing water or stabilizer.

Various surfactants can be incorporated into washing water or stabilizer used in the step of washing with water so as to prevent the formation of water spots in the course of drying of the processed photosensitive material. The surfactants include nonionic surfactants of polyethylene glycol type, nonionic surfactants of polyhydric alcohol type, anionic surfactants of alkylbenzenesulfonate type, anionic surfactants of higher alcohol sulfuric ester type, anionic surfactants of alkylnaphthalene sulfonate type, cationic surfactants of quaternary ammonium salt type, cationic surfactants of amine salt type, amphoteric surfactants of amino acid type and amphoteric surfactants of betaine type. Since ionic surfactants are bonded with various ions introduced by the process to form insoluble substances, the nonionic surfactants are desirable. Alkylphenol/ethylene oxide adducts are particularly preferred. Preferred examples of the alkylphenols include octyl-, nonyl-, dodecyl- and dinonylphenols. The molar number of added ethylene oxide is particularly preferably 8 to 14. In addition, silicon surfactants having a high defoaming effect are also preferably used.

The washing water and stabilizer can contain various antibacterial and antifungal agents in order to prevent the formation of scales or the formation of fungi on the processed photosensitive material. Examples of the antibacterial and antifungal agents include thiazolylbenzimidazole compounds described in J.P. KOKAI Nos. Sho 57-157244 and 58-105145; isothiazolone compounds described in J.P. KOKAI Nos. Sho 54-27424 and 57-8542; chlorophenol compounds typified by trichlorophenol; bromophenol compounds; organotin and organozinc compounds; thiocyanic acid and isothiocyanic acid compounds; acid amide compounds; diazine and triazine compounds; thiourea compounds; benzotriazole alkylguanidine compounds; quaternary ammonium salts typified by benzalkonium chloride; antibiotics typified by penicillin; and general-purpose antifungal agents described on pages 207 to 223 of J. Antibact. Antifung. Agents, Vol. 1, No. 5 (1983). Further, various antibacterial agents described in J.P. KOKAI No. sho 48-83820 are also usable.

Various chelating agents are also preferably used so far as they do not impair the effect of the compounds of the present invention. Preferred compounds as the chelating agent include, for example, aminopolycarboxylic acids such as ethylenediaminetetraacetic acid and diethylenetriaminepentaacetic acid; organophosphonic acids such as 1-hydroxyethylidene-1,1-diphosphonic acid and ethylenediamine-N,N,N',N'-tetramethylenephosphonic acid; and hydrolyzates of maleic anhydride polymers described in European Patent No. 345172A1.

Preservatives which can be contained in the fixing agent and bleach-fixing agent are preferably contained in the washing water.

The stabilizing solutions include, for example, solutions containing an organic acid, solutions having a buffering function and pH of 3 to 6, and solutions containing an aldehyde (such as formalin or glutaraldehyde), hexamethylenetetramine, hexahydrotriazine or an N-methylol compound (such as dimethylolurea or N-methylolpyrazole). If necessary, ammonium compounds such as ammonium chloride and ammonium sulfite; metal compounds such as Bi and Al compounds; fluorescent brightening agents; hardeners; and alkanolamines described in U.S. Pat. No. 4786583 are also usable.

The steps of washing with water and stabilization are preferably of multi-stage counter-current system. The number of the stages is preferably 2 to 4. The amount of the replenisher is 2 to 30 times, preferably 2 to 15 times, as much as that brought from the preceding bath per a unit area.

Water used in the water-washing step or stabilization step is city water or preferably water deionized to Ca and Mg concentrations of 5 mg/l or below with an ion-exchange resin or the like, or water sterilized with a halogen or a UV sterization lamp.

Although city water is usable for compensating for the evaporated water, the deionized water or sterilized water preferably used in the above water washing step or sterilization step is preferred.

In each of the processing solutions of the present invention, the stirring is conducted preferably as vigorously as possible. The vigorous stirring can be conducted by a method wherein a jet of the processing solution is bumped against the emulsion surface of the photosensitive material as described in J.P. KOKAI No. Sho 62-183460; a method wherein the stirring effect is improved with a rotating means as described in J.P. KOKAI No. Sho 62-18346; a method wherein the photosensitive material is moved while the emulsion surface thereof is brought into contact with a wiper blade or squeeze roller provided in the solution so as to make the flow on the emulsion surface turbulent and thereby improving the effect of the stirring; and a method wherein the quantity of the circulating flow of the whole processing solution is increased.

The process of the present invention is preferably conducted with an automatic developing machine. The transporting means in the automatic developing machine are described in J.P. KOKAI Nos. Sho 60-191257, 60-191258 and 60-191259. For rapidly conducting the process with the processing composition of the present invention, it is preferred to shorten the crossover between the processing tanks in the automatic developing machine. The automatic developing machine with which the crossover time is 10 seconds or shorter is described in J.P. KOKAI No. Hei 1-319038.

When the continuous process is conducted with the automatic developing machine by the processing method of the present invention, it is preferred that a replenisher is added in an amount depending on the amount of the processed photosensitive material so as to compensate for the ingredients of the processing solution spent for processing the photosensitive material and also to control the accumulation of undesirable ingredients eluted from the photosensitive material. Two or more processing tanks may be used in each processing step. In this case, a counterflow system wherein the replenisher flows from the subsequent bath into the preceding bath is preferred. A 2- to 4-stage cascade system is particularly preferred in the water washing step and stabilization step.

The amount of the replenisher is preferably as small as possible so far as the photographic properties are not impaired or other solutions are not stained by the change of the composition of each processing solution.

The amount of the repleniser for the color development is 100 to 1500 ml, preferably 100 to 1000 ml per square meter of the photosensitive material in processing the color photographic material; and is 20 to 220 ml, preferably 30 to 160 ml per square meter of the photosensitive material in processing the color printing material.

The amount of the repleniser for the bleaching is 10 to 500 ml, preferably 10 to 160 ml per square meter of the photosensitive material in processing the color photographic material; and is 20 to 300 ml, preferably 50 to 150 ml per square meter of the photosensitive material in processing the color printing material.

The amount of the repleniser for the bleach-fixing is 100 to 3000 ml, preferably 200 to 1300 ml per square meter of the photosensitive material in processing the color photographic material; and is 20 to 300 ml, preferably 50 to 200 ml per square meter of the photosensitive material in processing the color printing material. The bleaching composition can be fed together with the fixing composition as bleach-fixing composition; or the bleaching composition can be fed separately from the fixing composition; or the overflow from the bleaching bath and/or fixing bath can be mixed to obtain the bleach-fixing replenisher.

The amount of the replenisher for the fixing is 300 to 3000 ml, preferably 300 to 1000 ml per square meter of the photosensitive material in processing the color photographic material; and is 20 to 300 ml, preferably 50 to 200 ml per square meter of the photosensitive material in processing the color printing material.

The amount of the washing water or stabilizing solution to be replenished is 1 to 30 times, preferably 2 to 15 times, as much as that brought from the preceding bath per a unit area.

It is also preferred to combine various regeneration methods in order to further reduce the amount of the replenisher for protecting the environment. The processing solution can be regenerated while it is circulated in the automatic developing machine or, alternatively, the solution is once removed from the processing tank, properly regenerated and returned into the tank to use it again as the replenisher.

The developer can be regenerated by the ion-exchange with an anion exchange resin, removal of the deposits by, for example, electrodialysis and/or addition of a chemical called "regenerating agent". The regeneration rate is preferably at least 50%, and more preferably at least 70%. Commercially available anion exchange resins can be used and also ion exchangers of a high selectivity described in J. P. KOKAI No. Sho 63-11005 are preferably used.

The photographic sensitive materials which can be processed with the processing composition of the present invention include ordinary black-and-white silver halide photographic sensitive materials (such as black-and-white sensitive materials for photography, black-and-white sensitive materials for X-rays and black-and-white sensitive materials for printing), ordinary multi-layer silver halide color photographic sensitive materials (such as color negative films, color reversal films, color positive films, color negative films for movies, color printing papers, color reversal photographic papers and direct positive color printing papers), infrared sensitive materials for laser scanner, diffusion transfer sensitive materials (such as silver diffusion transfer sensitive materials and color diffusion transfer sensitive materials). The photographic sensitive materials according to the present invention may carry a magnetic record.

The following photosensitive materials can also be used preferably in the present invention.

The preferred photosensitive materials are those having a magnetic recording layer which comprises magnetic particles (preferably Co-coated ferromagnetic iron oxide) dispersed in a binder. Preferably, the layer is optically transparent and covering the whole surface of the photosensitive material. The magnetic particles may be treated with a coupling agent as described in J.P. KOKAI No. Hei 6-161032. As the binder, polymers described in J.P. KOKAI No. Hei 4-219569 are preferred. Although the position of the recording layer is not particularly limited, it is preferably on the back layer opposite to the emulsion layer side of the support. It is also preferred that there is a layer containing a lubricating agent on the recording layer, and that the outermost layer on the same side as the photosensitive emulsion layer side contains a matting agent.

The photosensitive material preferably contains an antistatic agent so that it still has the antistatic properties even after the completion of the development process. The antistatic agents are preferably conductive metal oxides and ionic polymers. The antistatic agents preferably have an electric resistance of no higher than $10^{12}$ Ω ·cm at 25° C. and 10% RH.

The photosensitive materials having the magnetic recording layer are described in U.S. Pat. Nos. 5,336,589, 5,250,404, 5,229,259 and 5, 215,874, and E.P. 466,130A.

The support for the photosensitive material is preferably a polyester support in the form of a thin layer and having improved curling tendency. The thickness of the support is preferably 50 to 105 µm, and the main starting material thereof is preferably a polyethylene aromatic dicarboxylate polyester (more preferably the one obtained by using benzenedicarboxylic acid or naphthalenedicarboxylic acid and ethylene glycol as main starting materials). The glass transition temperature of the support is preferably 50° to 200° C. The surface treatment of the support is conducted preferably by ultraviolet treatment, corona discharge treatment, glow discharge treatment or flame treatment. The support is preferably heat-treated at a temperature in the range of 40° C. to the glass transition temperature thereof for 0.1 to 1500 hours before or after the formation of a subbing layer thereon and before the formation of an emulsion layer. The support, photosensitive materials, development process, cartridge, etc. are described in Kokai-Giho (Published Technical Report) No. 94-6023 [published by Hatsumei Kyokai (Japan Institude of Invention and Innovation), 1994].

The photosensitive material of the present invention can have various layer constitutions (such as red-, green- and blue-sensitive silver halide emulsion layers, subbing layer, antihalation layer, filter layer, intermediate layer and surface-protecting layer) and arrangements on one or both surfaces thereof depending on the use of the photosensitive material.

Various color couplers can be used for the color photosensitive material in the process of the present invention. Examples of them are given in patents described in the above-described Research Disclosure No. 17643, VII-C to G and No. 307105, VII-C to G, J.P. KOKAI Nos. Sho 62-215272, Hei 3-33847, Hei 2-33144 and European Patent Publication Nos. 447969A and 482552A.

As yellow couplers, those described in the following specifications can be used so far as the effect of the present invention is not impaired: U.S. Pat. Nos. 3,933,501, 4,022,620, 4,326,024, 4,401,752 and 4,248,961, J.P. KOKOKU No. Sho 58-10739, British Patent Nos. 1,425,020 and 1,476,760, U.S. Pat. Nos. 3,973,968, 4,314,023, 4,511,649 and 5,118,599, European Patent Nos. 249,473A and 0,447,969, and J.P. KOKAI Nos. Sho 63-23145, Sho 63-123047, Hei 1-250944 and Hei 1-213648.

Particularly preferred yellow couplers include yellow couplers represented by general formula (Y) described in left upper column, page 18 to left lower column, page 22 of J.P. KOKAI No. Hei 2-139544; acylacetamide yellow couplers having a characteristic acyl group as described in J.P. KOKAI No. Hei 5-2248 and European Patent Publication No. 0447969 and yellow couplers represented by general formula (Cp-2) given in J.P. KOKAI No. Hei 5-27389 and European Patent Publication No. 0446863A2.

Preferred magenta couplers are 5-pyrazolone and pyrazoloazole compounds. More preferred are those described in U.S. Pat. Nos. 4,310,619 and 4,351,897, European Patent No. 73,636, U.S. Pat. Nos. 3,061,432 and 3,725,067, Research Disclosure No. 24220 (June, 1984), J.P. KOKAI No. Sho 60-33552, Research Disclosure No. 24230 (June, 1984), J.P. KOKAI Nos. Sho 60-43659, 61-72238, 60-35730, 55-118034 and 60-185951, U.S. Pat. Nos. 4,500, 630, 4,540,654 and 4,556,630, and International Publication No. WO 88/04795.

Particularly preferred magenta couplers are pyrazoloazole magenta couplers of general formula (I) described from right lower column, page 3 to right lower column, page 10 of J.P. KOKAI No. Hei 2-139544 and 5-pyrazolone magenta couplers of general formula (M-1) described from left lower column, page 17 to left upper column, page 21 of J.P. KOKAI No. Hei 2-139544. The most preferred are the above-described pyrazoloazole magenta couplers.

The cyan couplers include phenol and naphthol couplers. Those described in the following specifications are preferred: U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Disclosure No. 3,329,729, European Patent Nos. 0,121,365A and 249,453A, U.S. Pat. Nos. 3,446,622, 4,333, 999, 4,775,616, 4,451,559, 4,427,767, 4,690,889, 4,254,212 and 4,296,199 and J.P. KOKAI No. Sho 61-42658. Further, pyrazoloazole couplers described in J.P. KOKAI Nos. Sho 64-553, 64-554, 64-555 and 64-556, pyrrolotriazole couplers described in European Patent Publication Nos. 0,488, 248 and 0,491,197, pyrroloimidazole couplers described in European Patent Publication No. 0,456,226A, pyrazolopyrimidine couplers described in J.P. KOKAI No. Sho 64-46753, imidazole couplers described in U.S. Pat. No. 4,818,672 and J.P. KOKAI No. Hei 2-33144, cyclic active methylene-type cyan couplers described in J.P. KOKAI No. 64-32260, and couplers described in J.P. KOKAI Nos. Hei 1-183658, 2-262655, 2-85851 and 3-48243 are also usable.

Typical examples of the polymerized color-forming couplers are described in, for example, U.S. Pat. Nos. 3,451, 820, 4,080,211, 4,367,282, 4,409,320 and 4,576,910, British Patent No. 2,102,137 and European Patent No. 341,188A.

The couplers capable of forming a colored dye having a suitable diffusibility are preferably those described in U.S. Pat. No. 4,366,237, British Patent No. 2,125,570, European Patent No. 96,570 and West German Patent Publication No. 3,234,533.

Further, compounds which release a photographically useful residue during a coupling reaction are also preferably usable in the present invention. As DIR couplers which release a development inhibitor, those described in the patents shown in the above described RD 17643; VII-F as well as those described in J.P. KOKAI Nos. Sho 57-151944, 57-154234, 60-184248 and 63-37346 and U.S. Pat. Nos. 4,248,962 and 4,782,012 are preferred.

As the couplers which release a nucleating agent or a development accelerator in the image-form in the development step are preferably those described in British Patent Nos. 2,097,140 and 2,131,188 and J.P. KOKAI Nos. Sho 59-157638 and Sho 59-170840 are preferred.

Other couplers usable as the color photographic element of the present invention include competing couplers described in U.S. Pat. No. 4,130,427, polyequivalent couplers described in U.S. Pat. Nos. 4,283,472, 4,338,393 and 4,310,618, DIR redox compound-releasing couplers, DIR coupler-releasing couplers, DIR coupler-releasing redox compounds and DIR redox-releasing redox compounds described in J.P. KOKAI Nos. Sho 60-185950 and 62-24252, couplers which release a dye that restores the color after coupling-off as described in European Patent Nos. 173,302A, bleaching accelerator-releasing couplers described in RD Nos. 11449 and 24241 and J.P. KOKAI No. Sho 61-201247, ligand-releasing couplers described in U.S. Pat. No. 4,555,477, leuco dye-releasing couplers described in J.P. KOKAI No. Sho 63-75747 and fluorescent dye-releasing couplers described in U.S. Pat. No. 4,774,181.

The supports suitable for use in the present invention are such as those described in, for example, the above-describe RD No. 17643, p. 28 and RD No. 18716, right column on page 647 to left column on page 648.

Particularly when a color negative film is used, the preferred support is such that having a conductive layer and transparent magnetic layer on one surface thereof as described in J.P. KOKAI No. Hei 4-62543, that having a magnetic recording layer as described in WO 90/04205, FIG. 1A and that having a stripe magnetic recording layer and a transparent magnetic recording layer adjacent to the stripe magnetic recording layer as described in J.P. KOKAI No. Hei 4-124628. A protecting layer described in J.P. KOKAI No. Hei 4-73737 is preferably formed on these magnetic recording layers.

The thickness of the support is preferably 70 to 120 $\mu$m. As for the material of the support, various plastic films described from line 1, right upper column, page 5 to line 5, right upper column, page 6 of J.P. KOKAI No. Hei 4-124636 are usable. Preferred materials for the support include cellulose derivatives (such as diacetyl, triacetyl, propionyl, butanoyl and acetylpropionyl acetates), and polyesters (such as polyethylene terephthalate, poly-1,4-cyclohexane dimethylene terephthalate and polyethylene naphthalate) described in J.P. KOKOKU No. Sho 48-40414. Polyesters are preferred for the film support in the present invention since they have a higher draining effect.

The cartridge (patrone) for the color negative film of the present invention may be any of those used at present or known in the art. Those having a shape shown in FIGS. 1 to 3 of U.S. Pat. No. 4,834,306 or FIGS. 1 to 3 of U.S. Pat. No. 4,846,418 are particularly preferred.

The color negative films described from line 1, left upper column, page 14 to line 11, left lower column, page 18 of J.P. KOKAI No. Hei 4-125558 are preferably used for the present invention.

The present invention will be further illustrated by the following Examples, which by no means limit the invention.

EXAMPLE 1

A sample 101 which is a multilayer color negative film described in Example 1 of J.P. KOKAI No. Hei 5-303186 was prepared.

After the imagewise exposure of the sample 101 cut into a width of 35 mm, the sample was continuously processed with a processing solution which will be described below until the bleach fixing replenisher had become ten times as large as the tank capacity.

Silver was recovered from the bleach-fixing solution in a silver-recovering device arranged in line. A part of the overflow from the silver-recovering device was discharged as the waste, and the balance was regenerated and reused as the bleach-fixing replenisher. The silver-recovering device was a small electrolytic device having a carbon anode and stainless steel cathode. The current density was 0.5 A/dm$^2$. The rough sketch of the silver-recovering system is shown in FIG. 1 of J.P. KOKAI No. Hei 6-175305. Namely, an overflow 21 in a bleach-fixing tank 20 is directly introduced into a silver-recovering device 22, and an aliquot (100 ml/min) of the overflow is returned into the bleach-fixing tank 20 through a filter 24 by means of a pump 23. 300 ml/l of the overflow 25 from the silver-recovering device 22 is recovered into a regenerating tank 26. When the amount of the recovery has reached 1 l, air is introduced thereinto for about 2 hours, a regenerating agent 28 is added thereto and it is fed into a bleach-fixing replenisher tank 30 through a pump 29. The balance (100 ml) is discharged as a waste 27. The amount of the waste was 220 ml per square meter of the processed sample 101.

The water washing process was conducted in a counter-current cascade system with 5 stages of horizontally arranged water washing tanks arranged side by side. The apparatus used was that shown in FIG. 1 of J.P. KOKAI No. Hei 5-66540.

The overflow of the first washing water step $W_1$ was cascaded into the preceding bleach-fixing bath. A reverse osmosis membrane (RO) device RC 30 (a product of Fuji Photo Film Co., Ltd.) was arranged between the fourth water washing $W_4$ step and the fifth water washing $W_5$ step. Namely, the washing water from $W_4$ was treated with the RO device, and the concentrate was returned into $W_4$ step. A rough sketch of the processing machine is given in FIG. 2 of J.P. KOKAI Hei 6-175305. The processing steps ($N_{Blix}$) are shown below.

| (Step) | (Process time) | (Process temp.) | (Amount of replenisher)*1 | (Capacity of tank, l) |
|---|---|---|---|---|
| Color development | 110 sec | 45° C. | 104 ml | 2 |
| Bleach-fixing | 110 sec | 45° C. | 200 ml | 2 |
| Washing with water (1) | 15 sec | 45° C. | — | 0.5 |
| Washing with water (2) | 15 sec | 45° C. | — | 0.5 |
| Washing with water (3) | 15 sec | 45° C. | — | 0.5 |
| Washing with water (4) | 15 sec | 45° C. | — | 0.5 |
| Washing with water (5) | 15 sec | 45° C. | 104 ml | 0.5 |
| Stabilization | 2 sec | Room temp. | 30 ml | coating |
| Drying | 50 sec | 70° C. | — | — |

*1The amount of the replenisher was per m$^2$ of the photosensitive material.

The crossover time from the color development to the bleach-fixing and from bleach-fixing to washing with water (1) was 3 sec. The crossover time is included in the process time in the preceding bath. The average quantity of the processing solution taken out per m$^2$ of the photosensitive material was 65 ml.

The compensation for the evaporation was conducted by detecting the temperature and humidity of air outside the processing machine with a thermo-hygrometer and calculating the amount of the evaporated water as described in J.P. KOKAI No. Hei 3-280042. Water used for the compensation was ion-exchanged water which was the same as that used as water for washing in the above-described washing steps.

The composition of each of the processing solutions was as follows:

| (Color developer) | Mother liquor | Replenisher |
|---|---|---|
| Diethylenetriaminepentaacetic acid | 1.2 g | 4.0 g |
| 1-hydroxyethylidene-1,1-diphosphonic acid | 2.7 | 3.3 |
| Potassium hydroxide | 2.50 | 3.90 |
| Sodium sulfite | 3.84 | 9.0 |
| Sodium hydrogencarbonate | 1.8 | — |
| Potassium carbonate | 31.7 | 39.0 |
| Potassium bromide | 5.60 | — |
| Potassium iodide | 1.3 mg | — |
| Hydroxylamine sulfate | 2.5 | 6.9 |
| 2-Methyl-4-[N-ethyl-N-(β-hydroxyethyl)amino] aniline sulfate | 9.0 | 18.5 |
| Water | ad 1.0 l | 1.0 l |
| pH | 10.05 | 11.90 |

| (Bleach-fixing bath) | Mother liquor | Replenisher at start |
|---|---|---|
| Ammonium thiosulfate | 1.4 mol | 2.31 mol |
| Chelating agent shown in Table 1 | 0.17 | 0.28 |
| Ferric nitrate nonahydrate | 0.15 | 0.25 |
| Ammonium sulfite | 0.10 | 0.17 |
| m-Carboxybenzenesulfinic acid | 0.05 | 0.09 |
| Water | ad 1.0 l | 1.0 l |
| pH (25° C.) (adjusted with acetic acid and ammonia water) | 6.0 | 6.0 |
| (Bleach-fixing regenerating agent) (per liter of recovered solution to be regenerated) (g) | | |
| Ammonium thiosulfate | 0.91 | |
| Chelating agent shown in Table 1 | 0.11 | |
| Ferric nitrate nonahydrate | 0.10 | |
| Ammonium sulfite | 0.07 | |
| m-Carboxybenzenesulfinic acid | 0.04 | |

(Washing water) (common to mother liquid and replenisher)

Tap water was passed through a mixed bed column packed with an H-type strongly acidic cation exchange resin (Amberlite IR-120B; a product of Rohm & Haas Co.) and an OH-type strongly basic anion exchange resin (Amberlite IR-400; a product of Rohm & Haas Co.) to reduce calcium and magnesium ion concentration to 3 mg/l or below, and then 20 mg/l of sodium isocyanurate dichloride and 150 mg/l of sodium sulfate were added to the water. pH of the water was in the range of 6.5 to 7.5.

| (Stabilizer) (for coating) | (unit: g) |
|---|---|
| Formalin (37%) | 2.0 |
| Polyoxyethylene-p-monononylphenyl ether (average degree of polymerization: 10) | 0.3 |
| Disodium ethylenediaminetetraacetate | 0.05 |
| Water | ad 1.0 l |
| pH | 5.0 to 8.0 |

After processing 100 m$^2$ of Sample 101 in the above-described processing system, the amount of the waste was 22 liters.

The quantity of silver remaining in the highest density part of the multilayer color photosensitive material sample 101 processed as described above was determined by fluorescent X-ray analysis. The results are given in Table 1. $D_{min}$ value of each of the processed samples determined with green light (G light) were also read.

The same process as that described above was repeated except that the bleach-fixing step was replaced with four steps, i.e. bleaching—washing with water (A)—washing with water (B)—fixing and that the formulations of the processing solutions were changed as shown below.

| Step | Process time | Process temp. | Amount of replenisher |
|---|---|---|---|
| Bleaching | 3 min 00 sec | 38° C. | 710 ml |
| Washing with water (A) | 15 sec | 24° C. | countercurrent pipe system from (B) to (A) |
| Washing with water (B) | 15 sec | 24° C. | 430 ml |
| Fixing | 3 min 00 sec | 38° C. | 430 ml |

| (Standard bleaching solution) | Mother liquor | Replenisher |
|---|---|---|
| Ferric complex salt of sodium ethylenediaminetetraacetate trihydrate | 100.0 g | 120.0 g |
| Disodium ethylenediaminetetraacetate | 10.0 | 11.0 |
| 3-Mercapto-1,2,4-triazole | 0.03 | 0.08 |
| Ammonium bromide | 140.0 | 160.0 |
| Ammonium nitrate | 30.0 | 35.0 |
| Ammonia water (27%) | 6.5 ml | 4.0 ml |
| Water | ad 1.0 l | 1.0 l |
| pH (adjusted with ammonia water and nitric acid) | 6.0 | 5.7 |

| (Fixing solution) | Mother liquor | Replenisher |
|---|---|---|
| Disodium ethylenediaminetetraacetate | 0.5 g | 0.7 g |
| Ammonium sulfite | 20.0 | 22.0 |
| Aqueous ammonium thiosulfate soln. (700 g/l) | 295.0 ml | 320.0 ml |
| Acetic acid (90 %) | 3.3 | 4.0 |
| Water | ad 1.0 l | 1.0 l |
| pH (adjusted with ammonia water and acetic acid) | 6.7 | 6.8 |

$D_{min}$ value of the photosensitive material processed with the above-described standard bleaching solution was read. The difference in the $D_{min}$ value among the photosensitive materials, i.e. $\Delta D_{min}$ was determined on the basis of the $D_{min}$ value of the standard bleaching solution. The $D_{min}$ value obtained by using the standard bleaching solution was 0.60.

Bleach fog ($\bigcirc D_{min}$)=($D_{min}$ of sample $-(D_{min}$ of standard bleaching solution)

An increase in the stain during the storage of the processed photosensitive material under the following conditions was determined from the change in the density in the non-colored part before and after the storage by using the sample 101.

Dark, wet heat condition: 60° C., 70% RH, 4 weeks.

Stain increase ($\Delta D$)=($D_{min}$ after storage)−($D_{min}$ before storage)

To examine the degree of the poorness of recoloring, the sample 101 processed in the process step ($N_{Blix}$) was processed again in the following processing steps ($N_{BL}$):

| Step | Process time | Process temp. | Amount of replenisher*[1] |
|---|---|---|---|
| Bleaching | 3 min 00 sec | 38° C. | 710 ml |
| Washing with water (A) | 15 sec | 24° C. | countercurrent pipe system from (D) to (C) |
| Washing with water (D) | 15 sec | 24° C. | 430 ml |
| Fixing | 3 min 00 sec | 38° C. | 430 ml |
| Washing with water (6) | 15 sec | 45° C. | — |
| Washing with water (7) | 15 sec | 45° C. | — |
| Washing with water (8) | 15 sec | 45° C. | — |
| Washing with water (9) | 15 sec | 45° C. | — |
| Washing with water (10) | 15 sec | 45° C. | 104 ml |
| Stabilization | 2 sec | room temp. | 30 ml |
| Drying | 50 sec | 70° C. | — |

*[1]The amount of the replenisher was given per m² of the photosensitive material.

The above-described basic bleaching solution, water for washing, fixing solution and stabilizing solution were used for the bleaching, washing, fixing and stabilization, respectively.

$D_{max}$ values of the sample 101 before and after the above-described processing step ($N_{BL}$) as determined with red light (R light) were read.

Recoloring insufficiency ($D_{max}$)=($D_{max}$ after the process in $N_{BL}$) −($D_{max}$ of sample).

The stain of the back surface of the photosensitive material and clogging of the filter were observed as described below.

Stain: The emulsion-free surface of sample 101 was observed after the running to check the stain.

Evaluation:

◯: no stain

Δ: slight stain which is practically negligible

×: stain

Clogging of filter: The filter was taken out and the degree of clogging inside thereof was examined after the completion of the running.

Evaluation:

◯: scarce clogging

Δ: partial clogging

×: Substantially the whole filter was clogging, but the liquid could pass through the filter.

××: the complete clogging, and the liquid extremely difficultly passes through the filter.

The results are shown in Table 1.

TABLE 1

| No. | Chelating agent | Amount of residual silver μm/cm² | Bleaching fog ΔDmin(G) | Increase in stain ΔD(G) | Recoloring insufficiency ΔD$_{max}$ (R) | Stain | Filter clogging | Remarks |
|---|---|---|---|---|---|---|---|---|
| 101 | comp. compd. A | 48.5 | 0.00 | 0.01 | 0.00 | ◯ | ◯ | Comp. Ex. |
| 102 | comp. compd. B | 39.7 | 0.08 | 0.08 | 0.00 | X | XX | Comp. Ex. |
| 103 | comp. compd. C | 25.2 | 0.00 | 0.01 | 0.20 | ◯ | ◯ | Comp. Ex. |
| 104 | compound 1 | 5.2 | 0.00 | 0.01 | 0.00 | ◯ | ◯ | Present invention |

TABLE 1-continued

| | | | | | | | | | |
|---|---|---|---|---|---|---|---|---|---|
| 105 | compound 2 | 4.4 | 0.00 | 0.01 | 0.00 | ○ | ○ | Present invention |
| 106 | compound 3 | 7.5 | 0.01 | 0.01 | 0.00 | ○ | ○ | Present invention |
| 107 | compound 8 | 6.8 | 0.01 | 0.01 | 0.00 | ○ | ○ | Present invention |
| 108 | compound 19 | 7.9 | 0.01 | 0.01 | 0.00 | ○ | ○ | Present invention |
| 109 | compound 26 | 6.7 | 0.01 | 0.02 | 0.00 | ○ | ○ | Present invention |
| 110 | compound 32 | 5.1 | 0.00 | 0.01 | 0.00 | ○ | ○ | Present invention |
| 111 | compound 33 | 3.9 | 0.00 | 0.01 | 0.00 | ○ | ○ | Present invention |
| 112 | compound 38 | 8.1 | 0.01 | 0.02 | 0.00 | ○ | ○ | Present invention |
| 113 | compound 45 | 5.5 | 0.00 | 0.01 | 0.00 | ○ | ○ | Present invention |

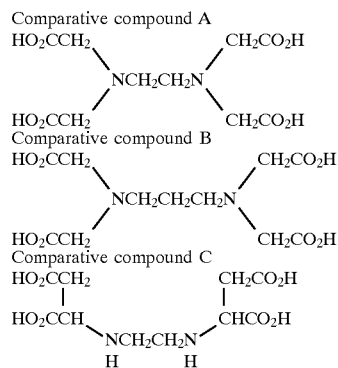

Comparative compound A

Comparative compound B

Comparative compound C

From Table 1, the superiority of the present invention is apparent in view of all of the desilvering properties, bleach fog, stain increase, insufficient recoloring, staining and filter clogging.

EXAMPLE 2

A multilayer color photographic paper (sample 001) described in Example 4 of J.P. KOKAI No. Hei 5-303186, and the following processing solutions were prepared:

| | Mother liquor | Replenisher |
|---|---|---|
| (Color developer) | | |
| Cation exchanged water | 800.0 ml | 800.0 ml |
| Compound A | 0.1 g | 0.1 g |
| Compound A | | |
| Triisopropanolamine | 15.0 g | 15.0 g |
| Potassium hydroxide | 3.0 g | 3.0 g |
| Ethylenediaminetetraacetic acid | 4.0 g | 4.0 g |
| Sodium 4,5-dihydroxybenzene-1,3-disulfonate | 0.5 g | 0.5 g |
| Potassium chloride | 14.5 g | — |
| Potassium bromide | 0.04 g | — |
| Fluorescent brightening agent (compound B) | 2.5 g | 3.0 g |
| Compound B | | |

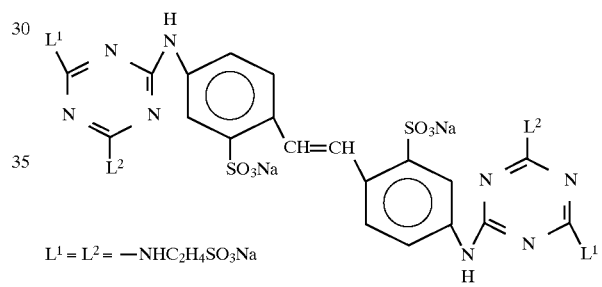

$L^1 = L^2 = $ —NHC$_2$H$_4$SO$_3$Na

| | | |
|---|---|---|
| Sodium sulfite | 0.1 g | 0.1 g |
| Disodium N,N-bis(sulfonatoethyl) hydroxylamine | 8.5 g | 11.0 g |
| N-Ethyl-N-(β-methanesulfonamidoethyl)-3-methyl-4-aminoaniline 3/2 sulfate monohydrate | 5.0 g | 11.5 g |
| Potassium carbonate | 26.3 g | 26.3 g |
| Water ad | 1.0 l | 1.0 l |
| pH | 10.15 | 11.15 |
| (Bleach-fixing bath) | | |
| Water | 700.0 ml | 700.0 ml |
| Ammonium thiosulfate (750 g/l) | 100.0 ml | 250.0 ml |
| Ammonium sulfite | 35.0 g | 88.0 g |
| p-Aminobenzenesulfinic acid | 5.0 g | 12.5 g |
| Imidazole | 8.0 g | 20.0 g |
| Chelating agent shown in Table 2 | 0.11 mol | 0.28 mol |
| Ferric nitrate nonahydrate | 40.4 g | 101 g |
| Water ad | 1.0 l | 1.0 l |
| pH (25° C.) (adjusted with acetic acid or ammonium water) | 7.0 | 6.8 |
| (Rinse) [common to (1) through (4)] | | |
| Sodium isocyanurate chloride | 0.02 g | 0.02 g |
| Deionized water (conductivity: not higher than 5 μS/cm) | 1000.0 ml | 1000.0 ml |
| pH | 6.5 | 6.5 |

-continued

Processing step ($P_{Blix}$):

| Processing step | Temp. | Time | Amount of replenisher* | Capacity of tank (l) |
|---|---|---|---|---|
| Color development | 39° C. | 45 sec | 7o ml | 20 |
| Bleach-fixing | 35° C.(1) | 45 sec | 60 ml** | 20 |
|  | (2) | 20 sec |  |  |
| Rinsing (1) | 35° C. | 20 sec | — | 10 |
| Rinsing (2) | 35° C. | 20 sec | — | 10 |
| Rinsing (3) | 35° C. | 20 sec | 360 ml* | 10 |
| Drying | 80° C. | 60 sec |  |  |

*The quantity of the replenisher was given per m² of the photosensitive material.
[The rinsing was conducted by counter-current method from (3) to (1) with three tanks.]
**120 ml, per m² of the photosensitive material, of the solution was replenished from the rinse (1) in addition to the above-mentioned 60 ml of the replenisher.

To determine the amount of silver remaining after the process, the multilayer color photographic paper (sample 001) was uniformly exposed so that the gray density became 2.2, and then processed in the same manner ($P_{Blix}$) as that described above. The amount of residual silver was determined by fluorescent X-ray method. To examine an increase in the stain, the gradation exposure-through-wedge was conducted and then the same procedure as that described above was repeated. The sample thus processed was kept at 80° C. and at 70% RH for one week, and the stain was determined before and after the process.

To examine Blix decoloring, the sample 001 was reprocessed by the following reprocessing steps $P_{EDTA}$ after the gradation exposure-through-wedge followed by the steps $P_{Blix}$. The degree of the Blix decoloring was determined by comparing the $D_{max}$ values determined with the red light (R light) before and after the reprocessing.

Reprocessing step ($P_{EDTA}$):

| Processing step | Temp. | Time | Amount of replenisher* | Capacity of tank (l) |
|---|---|---|---|---|
| Bleach-fixing | 35° C. | 45 sec | 60 ml** | 20 |
| Rinsing (4) | 35° C. | 20 sec | — | 10 |
| Rinsing (5) | 35° C. | 20 sec | — | 10 |
| Rinsing (6) | 35° C. | 20 sec | 360 ml* | 10 |
| Drying | 35° C. | 60 sec |  |  |

*The quantity of the replenisher was given per m² of the photosensitive material.
[The rinsing was conducted by counter-current method from (6) to (4) with three tanks.]
**120 ml, per m² of the photosensitive material, of the solution was replenished from the rinse (4) in addition to the above-mentioned 60 ml of the replenisher.

In the process ($P_{Blix}$), the mother liquor was fed into each processing tank to initiate the process in each step. The process was continued while the replenisher was fed into the tank, the quantity of the replenisher being changed as the process proceeded. The process was continued until the cumulative amount of the replenisher had reached three-times as large as the tank capacity. The results of the process thus conducted are shown in Table 2. In the reprocessing ($P_{EDTA}$), the above-described reprocessing steps $P_{EDTA}$ was repeated except that the chelating agent in the bleach-fixing solution was replaced with ethylenediaminetetraacetic acid. Other components were the same as those of $P_{Blix}$. In the reprocessing ($P_{EDTA}$), however, the respective solutions used were fresh.

TABLE 2

| No. | Chelating agent | Bleach-fixing time sec. | Quantity of residual silver μg/cm² | Stain ΔD(G) | Blix decoloring ΔD$_{max}$ (R) | Remarks |
|---|---|---|---|---|---|---|
| 201 | Comp. compd. A | 45 | 2.6 | 0.11 | 0.00 | Comp. Ex. |
|  |  | 20 | 8.0 | 0.20 | 0.00 |  |
| 202 | "B | 45 | 10.6 | 0.03 | 0.00 | " |
|  |  | 20 | 20.2 | 0.04 | 0.00 |  |
| 203 | "C | 45 | 1.8 | 0.03 | 0.19 | " |
|  |  | 20 | 4.1 | 0.04 | 0.15 |  |
| 204 | Compound 1 | 45 | 1.0 | 0.02 | 0.00 | present |
|  |  | 20 | 3.1 | 0.03 | 0.00 | invention |
| 205 | Compound 2 | 45 | 0.9 | 0.02 | 0.00 | present |
|  |  | 20 | 2.0 | 0.03 | 0.00 | invention |
| 206 | Compound 3 | 45 | 1.5 | 0.03 | 0.00 | present |
|  |  | 20 | 3.6 | 0.03 | 0.00 | invention |
| 207 | Compound 8 | 45 | 1.5 | 0.04 | 0.00 | present |
|  |  | 20 | 3.5 | 0.03 | 0.00 | invention |
| 208 | Compound 19 | 45 | 1.8 | 0.03 | 0.00 | present |
|  |  | 20 | 4.0 | 0.04 | 0.00 | invention |
| 209 | Compound 23 | 45 | 1.2 | 0.03 | 0.00 | present |
|  |  | 20 | 3.4 | 0.04 | 0.00 | invention |
| 210 | Compound 26 | 45 | 1.6 | 0.03 | 0.00 | present |
|  |  | 20 | 3.5 | 0.04 | 0.00 | invention |
| 211 | Compound 32 | 20 | 3.2 | 0.03 | 0.00 |  |
| 212 | Compound 33 | 45 | 0.7 | 0.01 | 0.00 | present |
|  |  | 20 | 1.6 | 0.02 | 0.00 | invention |
| 213 | Compound 46 | 45 | 1.0 | 0.03 | 0.00 | present |
|  |  | 20 | 3.1 | 0.04 | 0.00 | invention |

Comparative compounds A, B and C were the same as those used in Example 1.

It is apparent from Table 2 that the heavy metal chelate compounds of the present invention are superior to the comparative compounds in the desilvering properties, staining with the lapse of time after the process, and Blix decoloring. The effects of them are remarkable particularly when the bleach-fixing time is reduced. Namely, even when the bleach-fixing time is reduced to a half, the amount of residual silver was small before and after the running, and the prevention from staining with the lapse of time was excellent. In the tests with the comparative compounds, although the residual silver was scarcely found when the solution was used immediately after the preparation, the desilvering properties were seriously deteriorated and precipitation occurred as the running proceeded.

EXAMPLE 3

A sample 301 was prepared in the same manner as that described in Example 1 of J.P. KOKAI No. Hei 5-165176 except that the subbed cellulose triacetate film support used for the multi-color photosensitive material A prepared in Example 1 of J.P. KOKAI Hei 5-165176 was replaced with a polyethylene naphthalate support having a thickness of 100μm and having a stripe magnetic recording layer described in Example 1 of J.P. KOKAI No. Hei 4-124628 on the back surface thereof. The same test as that conducted for samples 101 and 111 in above-described Example 1 was repeated except that the sample 301 was used. The effects of the present invention could be obtained as in Example 1 of the present invention.

A sample 302 was prepared in the same manner as that of Example 1 of the present invention except that the support used for the multilayer color photosensitive material 101 was replaced with a support and a back layer of Sample No. I-3 in Example of J.P. KOKAI Hei No. 4-62543 and that it was coated with 15 mg/m² of $C_8F_{17}SO_2N(C_3H_7$ )CH$_2$COOK to form the second protective layer. The sample 302 was processed into a format shown in FIG. 5 of J.P. KOKAI No. Hei 4-62543, and the same tests as those of samples 101 and 111 in Example 1 of the present invention were conducted to obtain the effects of the invention as in Example 1.

EXAMPLE 4

The sample 101 was cut into a film having a width of 35 mm. After the filming with a camera, the sample was processed at a rate of 1 m$^2$/day for 15 days as will be described below (running process).

Each process was conducted with an automatic developing machine FP-560B (a product of Fuji Photo Film Co., Ltd.). The machine was remodeled so that the whole overflow from the bleaching bath was discharged into a waste tank without introducing it into the subsequent bath.

The processing steps and compositions are shown below.

| (Step) | (Process time) | (Process temp.) | (Amount of replenisher)* | (Capacity of tank) |
|---|---|---|---|---|
| Color development | 3 min 5 sec | 37.6° C. | 15 ml | 17 l |
| Bleaching | 50 sec | 38.0° C. | 5 ml | 5 l |
| Fixing (1) | 50 sec | 38.0° C. | — | 5 l |
| Fixing (2) | 50 sec | 38.0° C. | 8 ml | 5 l |
| Washing with water | 30 sec | 38.0° C. | 17 ml | 3.5 l |
| Stabilization (1) | 20 sec | 38.0° C. | — | 3 l |
| Stabilization (2) | 20 sec | 38.0° C. | 15 ml | 3 l |
| Drying | 1 min 30 sec | 60° C. | — | — |

Processing step

*The amount of the replenisher was given per 1.1 m of the photosensitive material having 35 mm width (corresponding to a film of 24 Ex.).

The stabilizing solution and fixing solution flowed countercurrently from (2) to (1). The whole of the overflowed water was introduced into the fixing bath (2). The amounts of the color developer brought into the bleaching step, that of the bleaching solution into the bleach-fixing step, that of the bleach-fixing solution into the fixing step and that of the fixing solution into the washing step were 2.5 ml, 2.0 ml, 2.0 ml and 2.0 ml, respectively, per 1. 1 m of the photosensitive material of 35 mm width. The crossover time was 6 seconds in each case. The crossover time was included in the process time in the preceding bath.

The open areas in the processing machine were 120 cm$^2$ for the color developer, 120 cm$^2$ for the bleaching solution and about 100 cm$^2$ for other processing solutions.

The composition of each of the processing solutions was as follows:

| | Mother liquor | Replenisher |
|---|---|---|
| (Color developer) | | |
| Diethylenetriaminepentaacetic acid | 2.2 g | 2.2 g |
| Disodium catechol-3,5-disulfonate | 0.3 | 0.3 |
| 1-Hydroxyethylidene-1,1-diphosphonic acid | 2.0 | 2.0 |
| Sodium sulfite | 3.9 | 5.5 |
| Potassium carbonate | 37.5 | 39.0 |
| Disodium N,N-bis(2-sulfoethyl) hydroxylamine | 2.0 | 2.0 |
| Potassium bromide | 1.4 | |
| Potassium iodide | 1.3 mg | — |
| Hydroxylamine sulfate | 2.4 | 3.6 |
| 2-Methyl-4-[N-ethyl-N-(β-hydroxyethyl) amino] aniline sulfate | 4.5 | 6.8 |
| Water | ad 1.0 l | 1.0 l |
| pH | 10.05 | 10.21 |
| (Bleaching solution) | | |
| Chelating agent 32 of the present invention | 0.18 g | 0.27 g |
| Ferric nitrate nonahydrate | 0.16 | 0.24 |
| Ammonium bromide | 70 | 105 |
| Glutaric acid | 93 | 140 |
| Water | ad 1.0 l | 1.0 l |
| pH (adjusted with ammonia water) | 4.6 | 4.2 |

[Mother liquor for fixing (1)]

A mixture of the above-described bleaching mother liquor and the following fixing mother liquor in a volume ratio of 7:93. (pH 7.0)

| (Fixing solution) | Mother liquor | Replenisher |
|---|---|---|
| Ammoniuin sulfite | 19 g | 57 g |
| Aqueous solution of ammonium thiosulfate (700 g/l) | 280 ml | 840 ml |
| Imidazole | 15 | 45 |
| Ammonium methanethiosulfonate | 40 | 120 |
| Ethylenediaminetetraacetate | 15 | 45 |
| Water | ad 1.0 l | 1.0 l |
| pH (adjusted with ammonia water and acetic acid) | 7.4 | 7.45 |

(Washing water) The same as that of Example 1
(Stabilizing solution) The same as that of Example 1.

After the completion of the running process, the amount of the residual silver in the highest density part was determined in the same manner as that of Example 1. The amount of the residual silver was 4.2 mg/cm$^2$, which suggested that the desilvering properties were excellent.

EXAMPLE 5

The clogging of the filter was observed by the everchanging test with the bleach-fixing solution of Example 1 at 35° C. for one week without passing the photosensitive material. The results are shown in Table 3.

TABLE 3

| No. | Chelating agent | Clogging of filter | Remarks |
|---|---|---|---|
| 501 | Comp. Compd. A | ○ | Comp. Ex. |
| 502 | "B | XX | " |
| 503 | "C | Δ | " |
| 504 | Compound 1 | ○ | Present invention |
| 505 | Compound 2 | ○ | " |
| 506 | Compound 3 | ○ | " |
| 507 | Compound 5 | ○ | " |
| 508 | Compound 8 | ○ | " |
| 509 | Compound 12 | ○ | " |
| 510 | Compound 15 | ○ | " |
| 511 | Compound 19 | ○ | " |
| 512 | Compound 26 | ○ | " |
| 513 | Compound 32 | ○ | " |
| 514 | Compound 33 | ○ | " |
| 515 | Compound 45 | ○ | " |

The comparative compounds B, C and D were the same as those used in Example 1, and the criteria of the determination of the clogging of the filter were also the same as those of Example 1. It is apparent from the results shown in Table 3 that the bleach-fixing composition of the present invention is superior to the comparative compounds in the clogging of filter with time.

EXAMPLE 6

A photosensitive layer described from line 20, left column, page 96 to page 114 of Published Technical Report No. 94-6023 [published by Hatsumei Kyokai (Japan Institute of Invention and Innovation)] was formed on a subbed cellulose triacetate film support by coating to obtain a sample 601 which was a multilayer color photosensitive material (color negative film).

After the continuous gradation wedge exposure at a color temperature of 4800 K, the sample 601 prepared as described above was subjected to a running process (until the cumulative amount of the replenisher for the developer had become three times as large as the tank capacity) by the steps and processing solutions described below.

Silver was recovered from the bleach-fixing solution in a silver-recovering device by in-line system. A part of the overflow from the silver-recovering device was discharged as the waste, and the balance was regenerated and reused as the bleach-fixing replenisher. The silver-recovering device was a small electrolytic device having a carbon anode and stainless steel cathode. The current density was 0.5 A/dm$^2$. The rough sketch of the silver-recovering system is shown in FIG. 1 of J.P. KOKAI No. Hei 6-175305. Namely, an overflow from a bleach-fixing tank was directly introduced into a silver-recovering device, and an aliquot (100 ml/min) of the overflow was returned into the bleach-fixing tank through a filter by means of a pump 1. 300 ml/l of the overflow from the silver-recovering device was recovered into a regenerating tank. When the amount of the recovered overflow had reached 1 l, air was introduced thereinto for about 2 hours, a regenerating agent is added thereto and it was fed into a bleach-fixing replenisher tank through a pump 2. The balance (100 ml) was discharged as a waste. The amount of the waste was 220 ml per square meter of the sample 601.

The water washing process was conducted in a countercurrent cascade system with 5 stages of horizontally arranged water washing tanks which were also arranged side by side. The apparatus used was that shown in FIG. 1 of J.P. KOKAI No. Hei 5-66540.

The overflow of the first washing water step $W_1$ was cascaded into the preceding bleach-fixing bath. A reverse osmosis membrane (RO) device RC 30 (a product of Fuji Photo Film Co., Ltd.) was arranged between the fourth water washing $W_4$ step and the fifth water washing $W_5$ step. Namely, the washing water from $W_4$ was treated with the RO device, and the concentrate was returned into $W_4$ step. The processing steps are shown below. A rough sketch of the processing machine is given in FIG. 2 of J.P. KOKAI No. Hei 6-175305.

| (Step) | (Process time) | (Process temp.) | (Amount of replenisher)*1 | (Capacity of tank, l) |
|---|---|---|---|---|
| Color development | 60 sec | 45° C. | 260 ml | 2 |
| Bleach-fixing | 60 sec | 40° C. | 200 ml | 2 |
| Washing with water (1) | 15 sec | 40° C. | — | 0.5 |
| Washing with water (2) | 15 sec | 40° C. | — | 0.5 |
| Washing with water (3) | 15 sec | 40° C. | — | 0.5 |
| Washing with water (4) | 15 sec | 40° C. | — | 0.5 |
| Washing with water (5) | 15 sec | 40° C. | 104 ml | 0.5 |
| Stabilization | 2 sec | Room temp. | 30 ml | coating |
| Drying | 50 sec | 70° C. | — | — |

*1 The amount of the replenisher was given per m$^2$ of the photosensitive material.

The crossover time from the color development to the bleach-fixing and from bleach-fixing to washing with water (1) was 3 sec. The average quantity of the processing solution taken out per m$^2$ of the photosensitive material was 65 ml.

The compensation for the evaporation was conducted by detecting the temperature and humidity of air outside the processing machine with a thermo-hygrometer and calculating the amount of the evaporated water as described in J.P. KOKAI No. Hei 3-280042. Water used for the compensation was ion-exchanged water which was the same as that used as water for washing in the above-described washing steps.

In order to evaluate a level on which the problem had been solved with the compounds of the present invention, pH of the color developer was varied to compulsorily established the states having a pH elevated by 0.2 (pH 10.25) and a pH lowered by 0.2 (pH 9.85). The tests were conducted as described below.

The composition of each of the processing solutions was as follows:

| (Color developer) | Mother liquor | Replenisher |
|---|---|---|
| Diethylenetriaminepentaacetic acid | 4.0 g | 4.0 g |
| Chelating agent (compound shown in Table 4) | 0.01 mol | 0.01 mol |
| Sodium sulfite | 4.0 | 6.0 |
| Potassium carbonate | 40.0 | 40.0 |
| Potassium bromide | 2.0 | — |
| Potassium iodide | 1.3 mg | — |
| 4-Hydroxy-6-methyl-1,3,3a,7-tetrazaindene | 0.14 | — |
| Disodium N,N-bis(sulfonatoethyl) hydroxylamine | 13.2 | 17.2 |
| 2-Methyl-4-[N-ethyl-N-(β-hydroxyethyl) amino aniline sulfate | 11.0 | 14.5 |
| Water | ad 1.0 l | 1.0 l |
| pH (adjusted with potassium hydroxide and sulfuric acid | 10.25 or 9.85 | 10.50 or 10.10 |

| (Bleach-fixing bath) | Mother liquor | Replenisher at start |
|---|---|---|
| Ferric ammonium 2-{[1-(carboxyethyl)-carboxymethyl-amino]ethyl} - carboxymethylaminobenzoate monohydrate | 0.08 mol | 0.13 mol |
| Ferric ammonium ethylenediamine-tetraacetate dihydrate | 0.10 | 0.17 |
| Aqueous ammonium thiosulfate solution (700 g/l) | 300 ml | 495 ml |
| Ammonium iodide | 2.0 | — |
| Ammonium sulfite | 0.10 | 0.17 |
| m-Carboxybenzenesulfinic acid | 0.05 | 0.09 |

-continued

| | | |
|---|---|---|
| Succinic acid | 0.10 | 0.17 |
| Water | ad 1.0 l | 1.0 l |
| pH (adjusted with acetic acid and ammonia water) | 6.0 | 5.5 |
| (Bleach-fixing regenerating agent) (per liter of recovered solution to be regenerated) (g) | | |
| Ferric ammonium 2-{[1-(carboxyethyl)-carboxymethyl-amino]ethyl}-carboxymethyl-aminobenzoate monohydrate | 0.05 mol | |
| Ferric ammonium ethylenediamine-tetraacetate dihydrate | 0.07 | |
| Aqueous ammonium thiosulfate solution (700 g/l) | 195 ml | |
| Ammonium sulfite | 0.07 | |
| m-Carboxybenzenesulfinic acid | 0.04 | |
| Succinic acid | 0.07 | |

(Washing water) (common to mother liquid and replenisher)

Tap water was passed through a mixed bed column packed with an H-type strongly acidic cation exchange resin (Amberlite IR-120B; a product of Rohm & Haas Co.) and an OH-type strongly basic anion exchange resin (Amberlite IR-400; a product of Rohm & Haas Co.) to reduce calcium and magnesium ion concentration to 3 mg/l or below, and then 20 mg/l of sodium isocyanate dichloride and 150 mg/l of sodium sulfate were added to the water. pH of the water was in the range of 6.5 to 7.5.

| (Stabilizer) (for coating) | (unit: g) |
|---|---|
| Sodium p-toluenesulfinate | 0.03 |
| Polyoxyethylene-p-mononylphenyl ether (average degree of polymerization: 10) | 0.2 |
| Disodium ethylenediaminetetraacetate | 0.05 |
| 1,2,4-Triazole | 1.3 |
| 1,4-Bis(1,2,4-triazol-1-ylmethyl)piperazine | 0.75 |
| Water | ad 1.0 l |
| pH | 5.0 to 8.0 |

The residual rates of the developing agent and hydroxylamine after the completion of the running process were determined by the analysis. Further, the precipitate in the color developing solution of pH 0.25 after the completion of the running process was observed. The results are summarized in Table 4.

TABLE 4

| | | Residual amount of main ingredient | |
|---|---|---|---|
| No. | Chelating agent | (pH 10.25) | (pH 9.85) |
| 601 | None | 39% | 52% |
| 602 | Diethylenetriaminepentaacetic acid | 42% | 60% |
| 603 | 1-Hydroxyethylidene-1,1-diphosphonic acid | 59% | 71% |
| 604 | Ethylenediaminedisuccinic acid | 41% | 62% |
| 605 | Compound 1 of the present invention | 78% | 80% |
| 606 | "2 | 83% | 86% |
| 607 | "10 | 76% | 77% |
| 608 | "11 | 84% | 86% |
| 609 | "19 | 77% | 80% |
| 610 | "26 | 73% | 75% |
| 611 | "32 | 79% | 83% |
| 612 | "33 | 84% | 86% |
| 613 | "34 | 69% | 74% |
| 614 | "45 | 78% | 82% |

TABLE 4-continued

| | Residual amount of hydroxylamine | | | |
|---|---|---|---|---|
| No. | (pH 10.25) | (pH 9.85) | Precipitation* | Remarks |
| 601 | 34% | 48% | XXX | Comp. Ex. |
| 602 | 38% | 55% | X | " |
| 603 | 54% | 68% | ○ | " |
| 604 | 38% | 54% | X | " |
| 605 | 77% | 79% | ○ | Present invention |
| 606 | 80% | 85% | ○ | " |
| 607 | 70% | 74% | ○ | " |
| 608 | 81% | 85% | ○ | " |
| 609 | 71% | 72% | ○ | " |
| 610 | 68% | 72% | ○ | " |
| 611 | 79% | 82% | ○ | " |
| 612 | 81% | 86% | ○ | " |
| 613 | 68% | 72% | ○ | " |
| 614 | 78% | 81% | ○ | " |

* ○ indicates that the solution contained no precipitate at all.
X indicates that the larger the numeral, the larger the amount of the precipitate in the solution.

It is apparent from Table 4 that when no chelating compound is added or an ordinary chelating agent is added, the effect of a satisfactory level cannot be obtained due to a change in pH in some cases, and that the great effect can be obtained only when the compound of the present invention is added.

EXAMPLE 7

A sample 702 was processed by the same processing steps and with the same processing solutions as those in Example 1 with a processing machine for motion picture film. The evaluation method was the same as that of Example 1.
(1) Materials for the support:
The support used in this Example was prepared as follows: PEN: 100 parts by weight of a commercially available poly(ethylene-2,6-naphthalate) and 2 parts by weight of Tinuvin P. 326 (a product of Geigy) were dried by an ordinary method, molten at 300° C. and extruded through a T-die. The obtained product was longitudinally elongated to 3.3 times at 140° C. and then transversely elongated to 3.3 times at 130° C. The product was heat-set at 250° C for 6 seconds. The glass transition temperature of the product was 120° C.
(2) Coating of subbing layer:
Both surfaces of the support prepared as described above were processed by corona discharge. Then a subbing layer was formed on the surface on a high-temperature side of the support at the time of stretching by coating with a subbing solution having a composition described below. The corona discharge process was conducted with a solid state corona processing machine 6KVA model (a product of Pillar Inc.). The support having 30 cm width was processed at a speed of 20 m/min. From the reading of the current and voltage, 0.375 KV·A·min/m$^2$ process was conducted. In the process, the discharge frequency was 9.6 KHz and the gap clearance between the electrode and guiding roll was 1.6 mm.

| | |
|---|---|
| Gelatin | 3 g |
| Distilled water | 250 ml |
| Sodium-α-sulfodi-2-ethylhexylsuccinate | 0.05 g |
| Formaldehyde | 0.02 g |

A subbing layer having the following composition was formed on the support TAC:

| | |
|---|---|
| Gelatin | 0.2 g |
| Salicylic acid | 0.1 g |
| Methanol | 15 ml |
| Acetone | 85 ml |
| Formaldehyde | 0.01 g |

(3) Coating of back layer:

The first, second and third back layers given below were formed by coating on the surface of the support on which the subbing layer had been formed.

a) The first back layer:

| | |
|---|---|
| Fine powder of Co-containing needle-like γ-iron oxide (in the form of dispersion in gelatin; average particle diameter: 0.08 μm) | 0.2 g/m² |
| Gelatin | 3 g/m² |
| Compound of the following chemical formula (a) | 0.1 g/m² |
| Compound of the following chemical formula (b) | 0.02 g/m² |
| Poly(ethyl acrylate) (average diameter: 0.08 μm) | 1 g/m² |

$(CH_2=CHSO_2NHCH_2CH_2NH)_2CO$  (a)

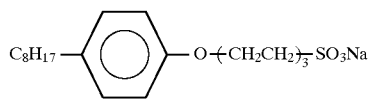  (b)

b) The second back layer:

| | |
|---|---|
| Gelatin | 0.05 g/m² |
| Conductive material [$S_n O_2/Sb_2O_3$ (9:1), particle diameter: 0.15 μm] | 0.16 g/m² |
| Sodium dodecylbenzenesulfonate | 0.05 g/m² | c) The third back layer:

| | |
|---|---|
| Gelatin | 0.5 g/m² |
| Polymethyl methacrylate (average particle diameter: 1.5 μm) | 0.02 g/m² |
| Cetyl stearate (dispersed in sodium dodecylbenzene sulfonate) | 0.01 g/m² |
| Disodium di(2-ethylhexyl)sulfosuccinate | 0.01 g/m² |
| Compound of the following chemical formula (c) | 0.01 g/m² |

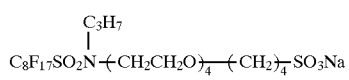  (c)

The coercive force of the obtained back layer was 960 Oe.

(4) Heat treatment of support:

After the formation of the subbing layer and back layers as described above followed by drying and rolling, the product thus obtained was heat-treated at 110° C. for 48 hours.

(5) Preparation of photosensitive layers:

A multi-layer color photosensitive material, i.e. sample 702, was prepared by forming photosensitive layers described from line 17, left column, page 116 to page 133 of Published Technical Report No. 94-6023 published by Hatsumei Kyokai (Japan Institute of Invention and Innovation), on the side opposite to the back layer obtained as described above.

The photosensitive material prepared as described above was cut into pieces having a width of 24 mm and length of 160 cm. Each piece was perforated to form two holes 2 mm across at an interval of 5.8 mm at one longitudinal end of the photosensitive material and 0.7 mm distant from the transverse edge thereof. The set of two holes was provided repeatedly at intervals of 32 mm. The photosensitive material was fitted in a film cartridge made from a plastic and shown in FIGS. 1 through 7 in U.S. Pat. No. 5,296,887.

The above-described sample 702 was then processed and evaluated in the same manner as that of Example 1 of the present invention. After the exposure and the processes, the sample 702 was again fitted in the plastic cartridge.

The excellent results were obtained also in the tests of the photosensitive material having the magnetic recording layer on the back surface, opposite to the emulsion layer, in the present invention as in Example 6.

EXAMPLE 8

A color paper of sample 001 in Example 4 of J.P. KOKAI No. Hei 50303186 was processed with processing solutions and processing methods described below.

In order to find a level on which the problem was solved with the compounds of the present invention, pH of the color developer was varied to compulsorily established the states having a pH elevated by 0.2 (pH 10.25) and a pH lowered by 0.2 (pH 9.85). The tests were conducted as described below.

| (Color developer) | |
|---|---|
| Water | 700 ml |
| Disodium 1,2-dihydroxybenzene-4,6-disulfonate | 4.0 g |
| Triethanolamine | 12.0 g |
| Potassium chloride | 1.5 g |
| Potassium bromide | 0.01 g |
| Potassium carbonate | 27.0 g |
| Fluorescent brightener (WHITEX 4; a product of Sumitomo Chemical Co., Ltd.) | 1.0 g |
| Sodium sulfite | 0.1 g |
| Disodium N,N-bis(sulfonatoethyl)hydroxylamine | 10.0 g |
| N-Ethyl-N-(β-methanesulfonamidoethyl)-3-methyl-4-aminoaniline sulfate | 5.0 g |
| Water | 1.0 l |
| pH (25° C.) | 10.25 or 9.85 |

The above-described color developer will be referred to as "sample 801". A compound of the present invention or a comparative compound in an amount shown in Table 5 was added to sample 801 to obtain samples 802 to 811.

| (Bleach-fixing bath) | |
|---|---|
| Water | 600 ml |
| Ammonium thiosulfate (700 g/l) | 100 ml |
| Ammonium sulfite | 40 g |
| Ferric ammonium ethylenediaminetetraacetate | 55 g |
| Ethylenediaminetetraacetic acid | 5 g |
| Ammonium bromide | 40 g |
| Nitric acid (67%) | 30 g |
| Water | ad 1000 ml |
| pH (25° C.)(adjusted with acetic acid and ammonia water) | 5.8 |

(Rinse)

Ion-exchanged water (each of calcium content and magnesium content was not higher than 3 ppm).

5 ppm of ferric ion and 150 ppm of calcium ion were added to each of the above-described color developers and the resultant mixture was left to stand in a beaker having a numerical aperture of 0.10 cm⁻¹ at 38° C. for 20 days.

The color photosensitive material was then subjected to the gradation exposure with a color separation filter for sensitometry and a sensitometer (FWH; a product of Fuji Photo Film Co., Ltd.). The exposing time and exposure were 0.1 second and 250 CMS, respectively.

After the completion of the exposure, the photosensitive material was processed with the fresh solution (immediately after the preparation) and aged color developer by the following steps:

| Processing Step | | | | |
|---|---|---|---|---|
| Processing step | Temp. | Time | Amount of replenisher* | Capacity of tank (l) |
| Color development | 35° C. | 45 sec | 161 ml | 17 |
| Bleach-fixing | 35° C. | 45 sec | 215 ml | 17 |
| Rinsing (1) | 35° C. | 20 sec | — | 10 |
| Rinsing (2) | 35° C. | 20 sec | — | 10 |
| Rinsing (3) | 35° C. | 20 sec | 360 ml | 10 |
| Drying | 80° C. | 60 sec | | |

*The quantity of the replenisher was given per $m^2$ of the photosensitive material.

The rinsing was conducted by counter-current method from (3) to (1) with three tanks.

The amount of the developing agent remaining in the aged solution was determined by the high-performance liquid chromatography. The formation of the precipitate in the color developing solution after the aging was also observed. The results are summarized in Table 5.

TABLE 5

| | | Residual amount of main ingredient | |
|---|---|---|---|
| No. | Chelating agent (amount) | (pH 10.25) | (pH 9.85) |
| 801 | None | 51% | 68% |
| 802 | Sodium hexametaphosphate (1 g/l) | 70% | 82% |
| 803 | 1-Hydroxyethylidene-1,1-diphosphonic acid (60%) (1.6 g/l) | 72% | 85% |
| 804 | Ethylenediaminetetraacetic acid (1 g/l) | 60% | 71% |
| 805 | Ethylenediaminedisuccinic acid (1 g/l) | 55% | 67% |
| 806 | Compound 1 of the present invention (1 g/l) | 78% | 83% |
| 807 | Compound 2 of the present invention (1 g/l) | 81% | 87% |
| 808 | Compound 11 of the present invention (1 g/l) | 84% | 89% |
| 809 | Compound 19 of the present invention (1 g/l) | 78% | 82% |
| 810 | Compound 33 of the present invention (1 g/l) | 82% | 87% |
| 811 | Compound 45 of the present invention (1 g/l) | 80% | 84% |

| No. | Precipitation* | Remarks |
|---|---|---|
| 801 | XXX | Comp. Ex. |
| 802 | XX | " |
| 803 | XX | " |
| 804 | ◯ | " |
| 805 | X | " |
| 806 | ◯ | Present invention |
| 807 | ◯ | " |
| 808 | ◯ | " |
| 809 | ◯ | " |
| 810 | ◯ | " |
| 810 | ◯ | " |

*◯ indicates that no precipitate was formed at all.
X indicates that the precipitate was formed. The larger the number of X, the more serious the precipitation.

It is apparent from Table 5 that when no chelating compound is added or an ordinary chelating agent is added, the effect of a satisfactory level cannot be obtained due to a change in pH in some cases, and that the main ingredient remains in an amount sufficient for exhibiting its capacity when the compound of the present invention is added. It is also apparent that the inhibition of the precipitation is remarkably improved as compared with the Comparative Examples.

Particularly when the conventional compounds are used, those having a remarkable effect of inhibiting the precipitation have a poor effect of preventing the precipitation, and when the developing agents are not easily decomposed, the precipitation cannot be completely inhibited.

It will be understood that, on the contrary, the compounds of the present invention are capable of forming a stable color developer without the formation of the precipitate.

EXAMPLE 9

The following processing solutions were prepared:

| (Color developer) | (unit: g) |
|---|---|
| Diethylenetriaminepentaacetic acid | 1.0 |
| Chelating compound (see Table 6) | 0.01 mol |
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-(N-ethyl-N-β-hydroxyethylamino)-2-methyl-aniline sulfate | 4.5 |
| Water | ad 1.0 l |
| pH | 10.05 |

5 ppm (in terms of ferric ion) of ferric chloride and 150 ppm (in terms of calcium ion) of calcium nitrate were added to the above-described color developer to obtain samples 901 to 912. 5 liters of each sample was fed into a rigid polyvinyl chloride vessel having a size of 10 cm (length)×25 cm (width)×30 cm (depth). The solution was kept at 38° C. for 30 days to conduct the aging test while 3 l/min of the solution was continuously circulated by means of a pump.

The vessel had a floating lid of 200 $cm^2$ covering the solution surface, and the area of the liquid surface exposed to air was 50 $cm^2$.

The multi-layer color negative photosensitive material (sample 101) described in Example 1 of J.P. KOKAI No. Hei 4-274236 was cut into a film having 35 mm width. After 5 CMS wedge exposure at a color temperature of 4800 K, it was processed by the following steps with the samples 901 to 912 immediately after the preparation (fresh solution) or after the aging test.

| (Processing method): | | |
|---|---|---|
| | Process time | Process temp. |
| Color developement | 3 min 15 sec | 38.0° C. |
| Bleaching | 50 sec | 38.0° C. |
| Fixing | 1 min 40 sec | 38.0° C. |
| Washing with water (1) | 30 sec | 38.0° C. |
| Washing with water (2) | 20 sec | 38.0° C. |
| Stabilization | 20 sec | 38.0° C. |

| (Bleaching solution) | (unit: g) |
|---|---|
| Ferric ammonium 1,3-propanediaminetetraacetate | 0.55 mol |
| Ammonium bromide | 85 |
| Ammonium nitrate | 20 |
| Glycolic acid | 55 |
| Water | ad 1.0 l |
| pH | 4.2 |

| (Fixing solution) | (unit: g) |
|---|---|
| Ferric ammonium ethylenediaminetetraacetate | 1.7 |
| Ammonium sulfite | 14.0 |
| Aqueous ammonium thiosulfate solution (700 g/l) | 260.0 ml |
| Water | ad 1.0 l |
| pH | 7.0 |

(Washing water)

Tap water was passed through a mixed bed column packed with an H-type strongly acidic cation exchange resin (Amberlite IR-120B; a product Of Rohm & Haas Co.) and an OH-type strongly anionic exchange resin (Amberlite IRA-400; a product of Rohm & Haas Co.) to reduce calcium and magnesium ion concentration to 3 mg/l or below, and then 20 mg/l of sodium isocyanurate dichloride and 150 mg/l of sodium sulfate were added to the water. pH of the water was in the range of 6.5 to 7.5.

| (Stabilizer) | (unit: g) |
|---|---|
| Sodium p-toluenesulfinate | 0.03 |
| Polyoxyethylene-p-monononylphenyl ether (average degree of polymerization: 10) | 0.2 |
| Disodium ethylenediaminetetraacetate | 0.05 |
| 1,2,4-Triazole | 1.3 |
| 1,4-(Bis(1,2,4-triazol-1-ylmethyl)piperazine | 0.75 |
| Water | ad 1.0 l |
| pH | 8.5 |

The B density obtained with the solution after the aging test was determined with X-light 310 type photographic densitometer. The exposure at this time was such that the B-density as determined with blue light (B light) after the process with fresh solution would be 2.5.

The difference $\Delta D_B$ in the B density between the aged solution and the fresh solution was determined. The residual rate of the developing agent after the aging and hydroxylamine were determined by the analysis. The precipitation in the color developer after the aging was also macroscopically examined. The results are shown in Table 6.

TABLE 6

| No. | Chelating agent | $\Delta D_{max}$ | Residual rate of main ingredient | Residual rate of hydroxyl-amine** | Precip-itate* |
|---|---|---|---|---|---|
| 901 | None | -0.5 | 60% | 20% | BBB |
| 902 | Ethylenediamine-tetraacetic acid | -0.4 | 62% | 30% | G |
| 903 | Ethylenediamine-tetramethylenephos-phonic acid | -0.05 | 88% | 70% | B |
| 904 | Compound 1 | -0.05 | 87% | 76% | G |
| 905 | Compound 2 | -0.04 | 90% | 77% | G |
| 906 | Compound 3 | -0.05 | 85% | 69% | G |
| 907 | Compound 8 | -0.07 | 83% | 70% | G |
| 908 | Compound 11 | -0.04 | 86% | 72% | G |
| 909 | Compound 19 | -0.05 | 87% | 73% | G |
| 910 | Compound 26 | -0.05 | 86% | 73% | G |
| 911 | Compound 32 | -0.05 | 88% | 76% | G |
| 912 | Compound 33 | -0.04 | 91% | 79% | G |
| 913 | Compound 43 | -0.05 | 86% | 73% | G |

*G represents no precipitate at all.
Larger the number of B's, the larger the amount of the precipitate.
**After the oxidation with iodine, sulfanilic acid and α-naphthylamine were added, and the red light thus obtained was determined by spectrophotometry.

It is apparent from Table 6 that although the prevention of the precipitation and the stability of the solution were insufficient when the ordinary chelating agent was used, the remarkable effect can be obtained by the addition of the compound of the present invention.

EXAMPLE 10

3 g/l of compound 1, 2, 3, 8, 11, 19, 26, 32, 33 or 43 of the present invention was added to the fixing bath in Example 9, and then ferric ion which corresponded to that brought from the preceding bleaching solution was added thereto to obtain samples 1001 to 1009. After aging these samples at 38° C. for 30 days while the numerical aperture was kept at 0.1 cm$^{-1}$, the turbidity of the solution was observed. After the aging, all the fixing baths containing the compound of the present invention kept the transparency to suggest that no precipitation had occurred, while a severe turbidity was observed in other cases.

EXAMPLE 11

The stabilizer used in Example 9 was employed as comparative sample 1101. 100 mg/l of each of the compounds 1, 2, 3, 11, 19, 26 and 32 was added to the sample 1101 to obtain samples 1102 to 1108. The sample 101 of the multi-layer color negative photosensitive material was processed with thus obtained stabilizer and fresh solutions such as color developer of sample 901 used in Example 9 in the same manner as that of Example 9. The multi-layer color negative photosensitive material 101 thus processed was aged at 45° C. and 70% RH for one week.

The increase in the magenta stain ($\Delta D_{min}$) by the aging was determined.

The results are shown in Table 7.

TABLE 7

| No. | Chelating agent | ΔDmin | Remarks |
|---|---|---|---|
| 1101 | None | 0.25 | comp. ex. |
| 1102 | Compound 1 | 0.09 | present invention |
| 1103 | Compound 2 | 0.08 | " |
| 1104 | Compound 3 | 0.13 | " |
| 1105 | Compound 11 | 0.09 | " |
| 1106 | Compound 19 | 0.11 | " |
| 1107 | Compound 26 | 0.11 | " |
| 1108 | Compound 33 | 0.08 | " |

It is apparent that when the stabilizer of the present invention containing the compound of the invention is used, the increase in the stain can be controlled and the storability of the image can be improved.

EXAMPLE 12

The biodegradability of each of EDTA and compounds 32, 33 and 45 of the present invention was examined by 302 Revised Zahn-Wellens test according to OECD Chemical Test Guideline. The compounds of the present invention were 70% biodegradable, while EDTA was scarcely biodegradable. It is understood from these results that the processing compositions of the present invention are preferred for maintaining the global environment.

Thus, according to the present invention, the oxidation or decomposition of the ingredients of the processing solutions by the metal ions can be inhibited, the formation of precipitates or sludges can be prevented even in a concentrated processing solution, and the function can be kept stable for a long period of time. In addition, the processes with processing agents excellent in the desilvering, photographic properties and image storability-after-the processing and substantially free from the environmental pollution have been made possible.

What is claimed is:

1. A method for processing a silver halide photosensitive material, which comprises the step of processing an imagewise-exposed silver halide photosensitive material in the presence of a compound of the general formula (I) or a heavy metal chelate thereof:

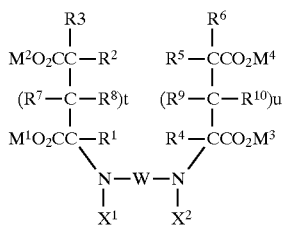

wherein $R^1$, $R^2$, $R^3$, $R^4$, $R^5$, $R^6$, $R^7$, $R^8$, $R^9$ and $R^{10}$ each represent a hydrogen atom, aliphatic group, aromatic group or hydroxyl group, W represents a divalent connecting group wherein the main chain has at most 5 carbon atoms, $X^1$ represents a hydrogen atom, alkyl group, hydroxyethyl group, alkoxyalkyl group, aralkyl group or hydroxyl group, $X^2$ represents an alkyl group, aralkyl group, hydroxyl group, hydroxyalkyl group or alkoxyalkyl group, $M^1$, $M^2$, $M^3$ and $M^4$ each represent a hydrogen atom or cation, and t and u each represent 0 to 5.

2. The method of claim 1 which comprises the steps of developing an imagewise-exposed silver halide photosensitive material and processing the material with a solution having a bleaching function which contains the compound of the general formula (I) or a heavy metal chelate thereof.

3. The method of claim 2 wherein $R^1$, $R^2$, $R^3$, $R^4$, $R^5$, $R^6$, $R^7$, $R^8$, $R^9$ and $R^{10}$ each represent a hydrogen atom, a linear, branched or cyclic alkyl, alkenyl or alkynyl group having 1 to 10 carbon atoms, a monocyclic or bicyclic aryl group or hydroxyl group, W represents a divalent connecting group wherein the main chain has at most 5 carbon atoms, $X^1$ represents a hydrogen atom, alkyl group having 1 to 5 carbon atoms, hydroxyethyl group, alkoxyalkyl group wherein the alkoxy has 1 to 6 carbon atoms and the alkyl has 1 to 6 carbon atoms, aralkyl group having 6 to 12 carbon atoms, or hydroxyl group, $X^2$ represents an alkyl group having 1 to 5 carbon atoms, aralkyl group having 6 to 12 carbon atoms, hydroxyl group, hydroxyalkyl group having 1 to 5 carbon atoms or alkoxyalkyl group wherein the alkoxy has 1 to 6 carbon atoms and the alkyl has 1 to 6 carbon atoms, $M^1$, $M^2$, $M^3$ and $M^4$ each represent a hydrogen atom or cation, and t and u each represent 0.

4. The method of claim 2 wherein W is represented by the following formula(W):

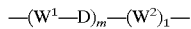

wherein $W^1$ and $W^2$ may be the same or different from each other, and the total carbon atoms in the main chain is at most 5, D represents —O—, —S— or —N($R_w$)—, $R_w$ represents a hydrogen atom, alkyl group having 1 to 8 carbon atoms or aryl group having 6 to 10 carbon atoms, m represents an integer of 0 to 3, and l represents an integer of 1 to 3.

5. The method of claim 2 wherein $R^1$, $R^2$, $R^3$, $R^4$, $R^5$, $R^6$, $R^7$, $R^8$, $R^9$ and $R^{10}$ each represent a hydrogen atom or hydroxyl group, W is represented by the following formula (W), $X^1$ represents a hydrogen or alkyl group having 1 to 5 carbon atoms, $X^2$ represents an alkyl group having 1 to 5 carbon atoms, aralkyl group having 6 to 12 carbon atoms, hydroxyl group, hydroxyalkyl group having 1 to 5 carbon atoms or alkoxyalkyl group wherein the alkoxy has 1 to 6 carbon atoms and the alkyl has 1 to 6 carbon atoms, $M^1$, $M^2$, $M^3$ and $M^4$ each represent a hydrogen atom or cation, and t and u each represent 0:

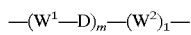

wherein $W^1$ and $W^2$ may be the same or different from each other, and the total carbon atoms in the main chain is at most 5, D represents —O—, —S— or —N($R_w$)—, $R_w$ represents a hydrogen atom, alkyl group having 1 to 8 carbon atoms or aryl group having 6 to 10 carbon atoms, m represents an integer of 0 to 3, and l represents an integer of 1 to 3.

6. The method of claim 2 wherein $R^1$, $R^2$, $R^4$, $R^5$, $R^7$, $R^8$, $R^9$ and $R^{10}$ each represent a hydrogen atom, $R^3$ and $R^6$ each represent a hydrogen atom or hydroxyl group, W is represented by the following formula (W), $X^1$ represents a hydrogen or alkyl group having 1 to 5 carbon atoms, $X^2$ represents an alkyl group having 1 to 5 carbon atoms, $M^1$, $M^2$, $M^3$ and $M^4$ each represent a hydrogen atom or cation, and t and u each represent 0 or 1:

wherein $W^1$ and $W^2$ may be the same or different from each other, and the total carbon atoms in the main chain is at most 5, D represents —O—, —S— or —N($R_w$)—, $R_w$ represents a hydrogen atom, alkyl group having 1 to 8 carbon atoms, m represents an integer of 0 or 1, and l represents an integer of 1.

7. The method of claim 2 wherin the compound is represented by the following general formula (III):

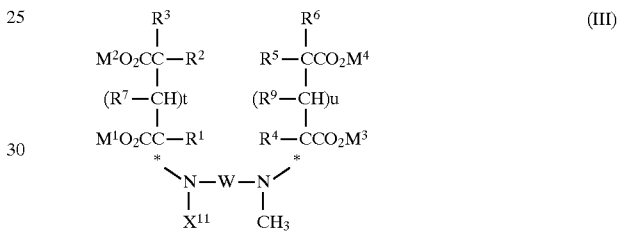

wherein $R^1$, $R^2$, $R^3$, $R^4$, $R^5$, $R^6$, $R^7$ and $R^9$ each represent a hydrogen atom or hydroxyl group, W is represented by the following formula (w), $X^{11}$ represents a hydrogen or methyl group $M^1$, $M^2$, $M^3$ and $M^4$ each represent a hydrogen atom or cation, and t and u each represent 0 to 5:

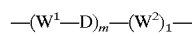

wherein $W^1$ and $W^2$ may be the same or different from each other, and the total carbon atoms in the main chain is at most 5, D represents —O—, —S— or —N($R_w$)—, $R_w$ represents a hydrogen atom, alkyl group having 1 to 8 carbon atoms or aryl group having 6 to 10 carbon atoms, m represents an integer of 0 to 3, and l represents an integer of 1 to 3.

8. The method of claim 2 wherein the compound is represented by the following general formula (IV)

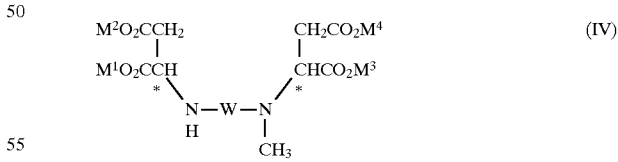

wherein W is represented by the following formula (W), and $M^1$, $M^2$, $M^3$ and $M^4$ each represent a hydrogen atom or cation:

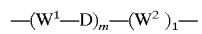

wherein $W^1$ and $W^2$ may be the same or different from each other, and the total carbon atoms in the main chain is at most 5, D represents —O—, —S— or —N($R_w$)—, $R_w$ represents a hydrogen atom, alkyl group having 1 to 8 carbon atoms or aryl group having 6 to 10 carbon atoms, m represents an integer of 0 to 3, and l represents an integer of 1 to 3.

9. The method of claim 7 wherein $R^1$, $R^2$, $R^4$, $R^5$, $R^7$ and $R^9$ each represent a hydrogen atom, $R^3$ and $R^6$ each represent a hydrogen atom or hydroxyl group, W is represented by the following formula (W), $X^{11}$ represents a hydrogen or methyl group, $M^1$, $M^2$, $M^3$ and $M^4$ each represent a hydrogen atom or cation, and t and u each represent 0 or 1:

$$—(W^1—D)_m—(W^2)_l—$$

wherein $W^1$ and $W^2$ may be the same or different from each other, and the total carbon atoms in the main chain is at most 5, D represents —O—, —S— or —N($R_w$)—, $R_w$ represents a hydrogen atom, alkyl group having 1 to 8 carbon atoms, m represents an integer of 0 or 1, and l represents an integer of 1.

* * * * *